(12) United States Patent
Saegusa

(10) Patent No.: US 11,801,430 B2
(45) Date of Patent: Oct. 31, 2023

(54) METHOD FOR MEASURING RIGIDITY CHARACTERISTICS AND SYSTEM FOR MEASURING RIGIDITY CHARACTERISTICS

(71) Applicant: PRGR Co., Ltd., Tokyo (JP)

(72) Inventor: Hiroshi Saegusa, Tokyo (JP)

(73) Assignee: PRGR Co., LTD., Tokyo (JP)

( * ) Notice: Subject to any disclaimer, the term of this patent is extended or adjusted under 35 U.S.C. 154(b) by 942 days.

(21) Appl. No.: 16/636,316

(22) PCT Filed: Apr. 5, 2018

(86) PCT No.: PCT/JP2018/014580
§ 371 (c)(1),
(2) Date: Feb. 3, 2020

(87) PCT Pub. No.: WO2019/030974
PCT Pub. Date: Feb. 14, 2019

(65) Prior Publication Data
US 2021/0162284 A1 Jun. 3, 2021

(30) Foreign Application Priority Data
Aug. 7, 2017 (JP) .................................. 2017-152295

(51) Int. Cl.
*A63B 60/42* (2015.01)
*A63B 53/04* (2015.01)
(Continued)

(52) U.S. Cl.
CPC .............. *A63B 60/42* (2015.10); *A63B 53/04* (2013.01); *G01N 3/303* (2013.01); *G01N 3/48* (2013.01);
(Continued)

(58) Field of Classification Search
CPC ........ A63B 60/42; A63B 53/04; G01N 3/303; G01N 3/48; G01N 2033/008; G01P 3/665
See application file for complete search history.

(56) References Cited

U.S. PATENT DOCUMENTS 6,837,094 B2 1/2005 Pringle et al.
2012/0010019 A1 1/2012 Curtis et al.
(Continued)

FOREIGN PATENT DOCUMENTS

JP H09-096598 4/1997
JP 2004-033626 2/2004
(Continued)

OTHER PUBLICATIONS

International Search Report for International Application No. PCT/JP2018/014580 dated Jun. 26, 2018, 4 pages, Japan.
(Continued)

*Primary Examiner* — Joshua T Kennedy
(74) *Attorney, Agent, or Firm* — Thorpe North & Western

(57) ABSTRACT

A system for measuring rigidity characteristics that measures a CT value of a golf club head based on an acceleration occurring in an impactor when the impactor is caused to strike the golf club head. Correlation data is calculated by measuring a representative CT value of the golf club head, which is calculated based on CT values measured multiple times by changing the impact velocity of the impactor, and a test velocity CT value, which is a CT value when the impact velocity is set to a predetermined test velocity, for each of a plurality of the golf club heads of an identical model. A rigidity characteristic value measuring device measures the test velocity CT value for another golf club head of the model. A computer estimates the representative CT value of the other golf club head based on the test velocity CT value and the correlation data.

20 Claims, 13 Drawing Sheets

(51) Int. Cl.
*G01N 3/303* (2006.01)
*G01N 3/48* (2006.01)
*G01P 3/66* (2006.01)
*G01N 33/00* (2006.01)

(52) U.S. Cl.
CPC ........ *G01P 3/665* (2013.01); *G01N 2033/008* (2013.01)

(56) References Cited

U.S. PATENT DOCUMENTS

2012/0264538 A1 10/2012 Curtis et al.
2013/0296071 A1 11/2013 Curtis et al.

FOREIGN PATENT DOCUMENTS

| JP | 2004-249086 | 9/2004 |
| JP | 2011-240043 | 12/2011 |
| JP | 2012-050807 | 3/2012 |

OTHER PUBLICATIONS

Technical Description of the Pendulum Test (Revised Version), The Royal and Ancient Golf Club of St Andrews and United States Golf Association, Nov. 2003, 38 pages, United States.

No.1  No.2

No.3  No.4

No.5  No.6

No.7  No.8

No.9  No.10

| NO | REPRESENTATIVE CT VALUE | SLOPE | CT(VL) | CT(VM) | CT(VH) |
|----|---|---|---|---|---|
| 1 | 247.3 | 5.28 | 252.2 | 252.2 | 253.3 |
| 2 | 247.6 | 5.23 | 252.3 | 253.0 | 253.7 |
| 3 | 247.3 | 7.57 | 254.3 | 255.0 | 256.3 |
| 4 | 247.3 | 6.97 | 253.5 | 254.5 | 255.1 |
| 5 | 259.0 | 5.05 | 263.6 | 264.1 | 264.8 |
| 6 | 253.7 | 6.86 | 259.8 | 260.7 | 261.5 |
| 7 | 254.6 | 6.30 | 259.8 | 261.1 | 261.4 |
| 8 | 250.8 | 7.72 | 257.6 | 258.8 | 259.4 |
| 9 | 255.2 | 5.24 | 259.9 | 260.6 | 261.2 |
| 10 | 255.8 | 7.22 | 262.1 | 263.4 | 263.9 |

| NO | REPRESENTATIVE CT VALUE | TEST VELOCITY CT VALUE | CONVERTED REPRESENTATIVE CT VALUE | DEVIATION |
|----|---|---|---|---|
| 1 | 247.3 | 260.3 | 246.1 | -1.2 |
| 2 | 247.6 | 261.0 | 246.7 | -0.9 |
| 3 | 247.3 | 263.5 | 249.2 | 1.9 |
| 4 | 247.3 | 262.7 | 248.4 | 1.1 |
| 5 | 259.0 | 273.0 | 258.5 | -0.5 |
| 6 | 253.7 | 268.4 | 253.9 | 0.2 |
| 7 | 254.6 | 268.3 | 253.9 | -0.7 |
| 8 | 250.8 | 266.4 | 252.0 | 1.2 |
| 9 | 255.2 | 267.8 | 253.4 | -1.8 |
| 10 | 255.8 | 271.2 | 256.7 | 0.9 |

METHOD FOR MEASURING RIGIDITY CHARACTERISTICS AND SYSTEM FOR MEASURING RIGIDITY CHARACTERISTICS

TECHNICAL FIELD

The present technology relates to a system for measuring rigidity characteristics of an object to be impacted.

BACKGROUND ART

In the related art, there is known a technique for measuring a CT (characteristic time) value being a rigidity characteristic value as an indicator that affects rebounding performance of a striking tool such as a golf club head.

In particular, for a golf club for competitive use, a CT value is measured by a pendulum test defined by the United States Golf Association (USGA). The procedure and the like of the pendulum test are described in detail in "Technical Description of the Pendulum Test (Revised Version)", The Royal and Ancient Golf Club of St Andrews and the United States Golf Association, November 2003.

U.S. Pat. No. 6,837,094 describes an apparatus for performing the pendulum test above, in which a golf club the head and the shaft of which are integrated is fixed, and a metallic spherical body on a pendulum strikes the face surface. The spherical body is equipped with an acceleration sensor, and a parameter indicating the rigidity characteristics thereof is calculated from a detected value of the acceleration sensor.

Japan Unexamined Patent Publication No. 2004-33626 describes a method of striking a face surface of a golf club head with an impact hammer and, using a computer, measuring a time at which the acceleration of the impact hammer first decreases to zero immediately after striking. The measured time is then determined for each measurement position, and a distribution of the times is determined to get a rigidity distribution of the golf club head. This enables the rigidity distribution of the golf club head to be measured easily and accurately.

Golf clubs for competitive use each have a compatible range (more specifically, an upper limit value) of a CT value determined. When the CT value of a golf club is measured to determine whether it is within a compatible range, a representative CT value of the golf club head needs to be calculated based on CT values measured at a plurality of impact velocities (generally three velocity levels), and the representative CT value needs to be determined whether it is within the compatible range.

Unfortunately, when total inspection is performed in a manufacturing process of golf clubs, for example, there is a problem in that inspection performed by measurement at a plurality of impact velocities takes time.

In addition, since an object to be inspected is a product to be shipped, the inspection in the manufacturing process of golf clubs that may cause a flaw or the like in the product is to be avoided as much as possible. However, there is a problem in that a flaw or the like may occur in the golf club in measurement at the plurality of impact velocities, particularly from an impact at a high velocity.

SUMMARY

The present technology measures rigidity characteristics of an object to be impacted in a short time.

A method for measuring rigidity characteristics according to a first aspect of the present technology is configured to measure a rigidity characteristic value based on an acceleration occurring in an impactor when the impactor is caused to strike an object to be impacted, the method including the steps of: 1) calculating a representative characteristic value of the object to be impacted based on the rigidity characteristic values measured multiple times by changing an impact velocity of the impactor; 2) measuring a test velocity characteristic value, which is the rigidity characteristic value at the impact velocity set to a predetermined test velocity; 3) calculating a correlation between the representative characteristic value and the test velocity characteristic value by performing the steps 1) and 2) on a plurality of objects to be impacted belonging to a group of objects to be impacted that are each predicted to have a substantially identical velocity dependence of the rigidity characteristic value; 4) actually measuring the test velocity characteristic value for another object to be impacted belonging to the group of objects to be impacted; and 5) estimating the representative characteristic value of the other object to be impacted based on the test velocity characteristic value measured in the step 4) and the correlation calculated in the step 3).

The method for measuring the rigidity characteristics according to a second aspect of the present technology is configured such that the object to be impacted is a mass-produced product, the group of objects to be impacted that are each predicted to have the substantially identical velocity dependence of the rigidity characteristic value are products of an identical model, and in the step 3), the correlation is calculated for each product of the identical model.

The method for measuring the rigidity characteristics according to a third aspect of the technology is configured such that the rigidity characteristic value is predicted to take a different value for each impact position of the impactor against the object to be impacted, and in the step 3), the correlation is calculated for each reference impact position defined for corresponding each of the products of the identical model.

The method for measuring the rigidity characteristics according to a fourth aspect of the present technology is configured such that a predetermined compatible range is set for the representative characteristic value, and the method further includes the step of 6) determining whether the representative characteristic value of the other object to be impacted, estimated in the step 5), is within the compatible range.

The method for measuring the rigidity characteristics according to a fifth aspect of the present technology further includes the step of 7) presenting a determination result in the step 6) to a measurer.

The method for measuring the rigidity characteristics according to a sixth aspect of the present technology is configured such that the test velocity is defined as a test velocity range including an upper limit velocity and a lower limit velocity, and in the step 4), measurement is performed at the impact velocity falling within the test velocity range.

The method for measuring the rigidity characteristics according to a seventh aspect of the present technology is configured such that the test velocity is set to a lowest velocity of a plurality of the impact velocities in the step 1).

The method for measuring the rigidity characteristics according to an eighth aspect of the present technology is configured such that the rigidity characteristic value is measured by using a rigidity characteristic value measuring device, in the step 1), the rigidity characteristic value is measured by using a rigidity characteristic value measuring device of a first type, and in the steps 2) and 4), the rigidity characteristic value is measured by using a rigidity characteristic value measuring device of a second type different from the rigidity characteristic value measuring device of the first type.

The method for measuring the rigidity characteristics according to a ninth aspect of the present technology is configured such that the rigidity characteristic value measuring device of the first type is configured to cause the impactor to strike the object to be impacted using a pendulum, and the rigidity characteristic value measuring device of the second type is configured to cause the impactor to strike the object to be impacted by dropping the impactor vertically.

The method for measuring the rigidity characteristics according to a tenth aspect of the present technology is configured such that the object to be impacted is a golf club head, and the rigidity characteristic value is a CT value of the golf club head.

A system for measuring rigidity characteristics according to an eleventh aspect of the present technology is configured to measure a rigidity characteristic value of an object to be impacted based on an acceleration occurring in an impactor when the impactor strikes the object to be impacted, the system including: a rigidity characteristics measuring unit that measures correlation data between a representative characteristic value of the object to be impacted, which is calculated based on the rigidity characteristic values measured multiple times by changing an impact velocity of the impactor, and a test velocity characteristics value, which is the rigidity characteristic value at a predetermined test velocity set to the impact velocity, for each of a plurality of objects to be impacted belonging to a group of objects to be impacted that are each predicted to have a substantially identical velocity dependence of the rigidity characteristic value, and that measures the test velocity characteristic value for another object to be impacted belonging to the group of objects to be impacted; and a representative characteristic value estimation unit that estimates the representative characteristic value of the other object to be impacted based on the test velocity characteristic value measured by the rigidity characteristics measuring unit and the correlation data.

The system for measuring the rigidity characteristics according to a twelfth aspect of the present technology is configured such that the object to be impacted is a mass-produced product, and the group of objects to be impacted that are each predicted to have the substantially identical velocity dependence of the rigidity characteristic value are products of an identical model, the correlation data being calculated for each model of the products.

The system for measuring the rigidity characteristics according to a thirteenth aspect of the present technology is configured such that the rigidity characteristic value is predicted to take a different value for each impact position of the impactor against the object to be impacted, and the correlation data is calculated for each reference impact position defined for corresponding each of the models.

The system for measuring the rigidity characteristics according to a fourteenth aspect of the present technology is configured such that a predetermined compatible range is set for the representative characteristic value, and the system further includes a compatibility determination unit that determines whether the representative characteristic value of the other object to be impacted, estimated by the representative characteristic value estimation unit, falls within the compatible range.

The system for measuring the rigidity characteristics according to a fifteenth aspect of the present technology further includes a determination result presenting unit that presents a determination result in the compatibility determination unit to a measurer.

The system for measuring the rigidity characteristics according to a sixteenth aspect of the present technology is configured such that the test velocity is defined as a test velocity range including an upper limit velocity and a lower limit velocity, and the rigidity characteristics measuring unit performs measurement at the impact velocity falling within the test velocity range.

The system for measuring the rigidity characteristics according to a seventeenth aspect of the present technology is configured such that the test velocity is set to a lowest velocity of a plurality of the impact velocities when the representative characteristic value is calculated.

The system for measuring the rigidity characteristics according to an eighteenth aspect of the present technology is configured such that the representative characteristic value of the correlation data is measured by using a rigidity characteristic value measuring device of a first type, and the test velocity characteristic value of the correlation data is measured by using a rigidity characteristic value measuring device of a second type different from the rigidity characteristic value measuring device of the first type, the rigidity characteristics measuring unit being the rigidity characteristic value measuring device of the second type.

The system for measuring the rigidity characteristics according to a nineteenth aspect of the present technology is configured such that the rigidity characteristic value measuring device of the first type has a mechanism of causing the impactor to strike the object to be impacted using a pendulum, and the rigidity characteristic value measuring device of the second type has a mechanism of causing the impactor to strike the object to be impacted by dropping the impactor vertically.

The system for measuring the rigidity characteristics according to a twentieth aspect of the present technology is configured such that the object to be impacted is a golf club head, and the rigidity characteristics value is a CT value of the golf club head.

According to the first or eleventh aspect of the present technology, the correlation between the representative characteristic value and the test velocity characteristic value is preliminarily calculated, and the representative characteristic value is estimated by measuring only the test velocity characteristic value at actual measurement. Accordingly, the representative characteristic value that normally needs to be measured multiple times by changing the impact velocity can be estimated by measurement at one test velocity, so the representative characteristic value can be measured in a short time.

According to the second or twelfth aspect of the present technology, the correlation is calculated for each product of an identical model, so that it is advantageous for efficiently measuring representative characteristic values of many objects to be impacted, such as when total inspection is performed on mass-produced products.

According to the third or thirteenth aspect of the present technology, the correlation is calculated for each reference impact position defined for respective products of an identical model, so it is advantageous for a case where one model has a plurality of management points (portions with a high possibility of falling out of the compatible range).

According to the fourth or fourteenth aspect of the present technology, it is determined whether the representative characteristic value of an object to be impacted of a measurement object is within a compatible range, so it is advantageous for performing quality control on the object to be impacted.

According to the fifth or fifteenth aspect of the present technology, a determination result whether the representative characteristic value is within a compatible range is presented, so it is advantageous for performing quality control on an object to be impacted.

According to the sixth or sixteenth aspect of the present technology, the test velocity is defined as the test velocity range including the upper limit velocity and the lower limit velocity, so it is advantageous in that while a predetermined deviation is allowed with respect to the impact velocity of the impactor, the deviation is prevented from exceeding a range in which the correlation is available.

According to the seventh or seventeenth aspect of the present technology, the test velocity is set relatively low, so it is advantageous for avoiding a flaw or the like caused in a surface to be impacted due to impact by measurement when an object to be impacted is a product to be shipped.

According to the eighth or eighteenth aspect of the present technology, the representative characteristic value is measured by using a rigidity characteristic value measuring device of a first type, and the test velocity characteristic value is measured by using a rigidity characteristic value measuring device of a second type, so the representative characteristic value can be measured efficiently, for example, by using an apparatus requiring complicated measurement but providing high accuracy as the rigidity characteristic value measuring device of the first type and by using an apparatus providing an easy measurement as the rigidity characteristic value measuring device of the second type.

According to the ninth or nineteenth aspect of the present technology, the rigidity characteristic value measuring device of the second type used at actual measurement (measurement by the rigidity characteristics measuring unit) is configured to drop the impactor vertically toward an object to be impacted, so an impact position and an impact angle of the impactor can be easily maintained in a constant manner, and thus it is advantageous for improving the measurement accuracy of the rigidity characteristics.

According to the tenth or twentieth aspect of the present technology, the CT value important for an evaluation indicator of a golf club head can be measured in a short time.

DETAILED DESCRIPTION

Hereinafter, a method for measuring rigidity characteristics and a system for measuring the rigidity characteristics according to preferred embodiments of the present technology will be described in detail with reference to the accompanying drawings.

In the present embodiment, an object to be impacted is a golf club head 30, and a CT value of the golf club head 30 is measured as a rigidity characteristic value.

In the present embodiment, the golf club head 30 is a mass-produced product, and representative CT values (representative characteristic values) of a plurality of the golf club heads 30 mass-produced are measured. Then, the representative CT values are evaluated whether each representative CT value is within a predetermined compatible range (rule compatible range).

Generally, products of an identical model (model number) are expected to have substantially identical performance. That is, a golf club head of an identical model is predicted to have a substantially identical representative CT value. However, mass-produced products have deviations, and actual representative CT values are normally distributed. In particular, when a predicted representative CT value is close to an upper limit value or a lower limit value in a compatible range, there is a need to check a representative CT value for each of the golf club heads 30.

Accordingly, in the present embodiment, it is assumed that a representative CT value is measured for the plurality of golf club heads 30, such as total inspection of mass-produced products.

Figure 4:
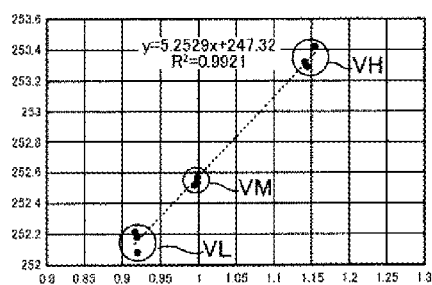
FIG. 4 is examples of graphs showing measurement results of a CT value of a golf club head 30.
Figure 4:
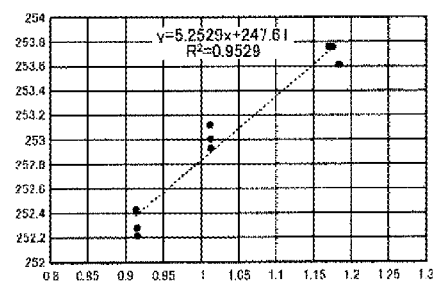
Figure 4:
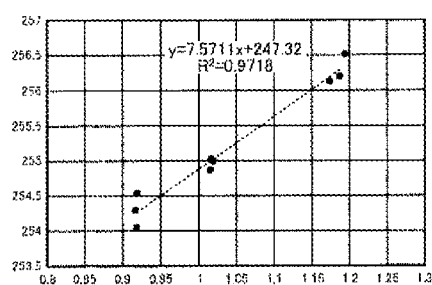
Figure 4:
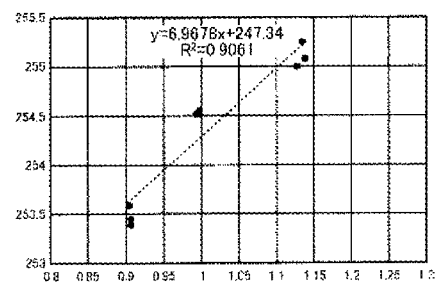
Figure 4:
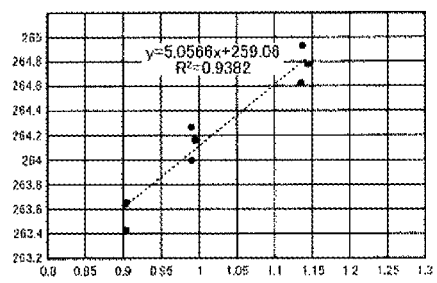
Figure 4:
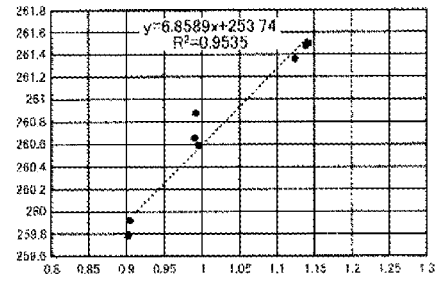
Figure 4:
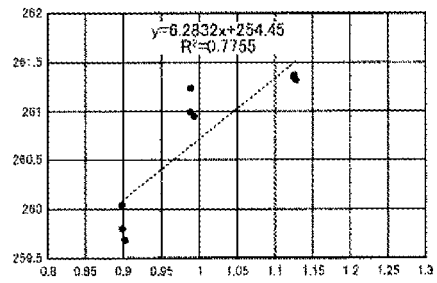
Figure 4:
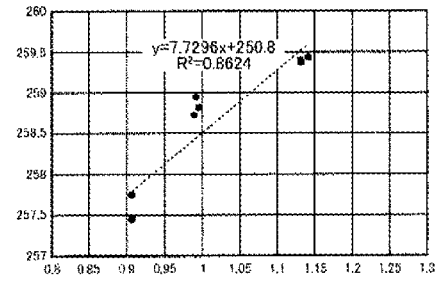
Figure 4:
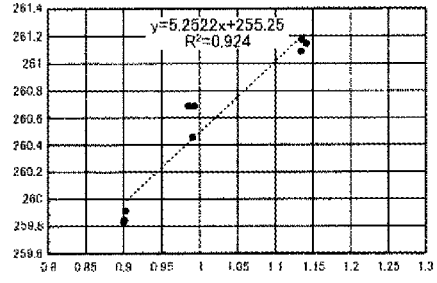
Figure 4:
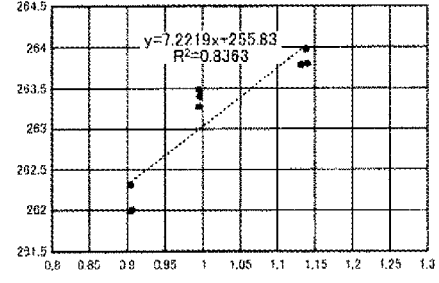

Here, the CT value measured in the present embodiment is known to be velocity dependent. In other words, as illustrated in FIG. 4 and the like described below, the CT value varies depending on an impact velocity of an impactor, and there is a certain correlation between the impact velocity and the CT value.

The present embodiment focuses on a fact that each of the CT values has substantially identical velocity dependency (the slope of each graph in FIG. 4), even though golf club heads of an identical model measured at an identical measurement position have a deviation in CT values. From this, the representative CT value, which normally needs to be measured multiple times by changing the impact velocity, is estimated from a measured value at one test velocity.

Structure of Golf Club Head 30

First, the structure of the golf club head 30 will be described.

Figure 14:
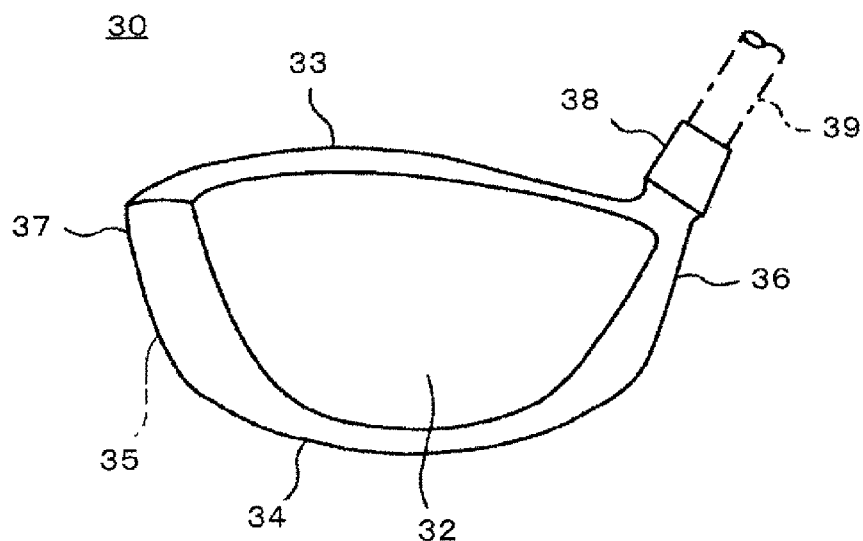
FIG. 14 is a diagram illustrating a structure of a golf club head 30.

As illustrated in FIG. 14, the golf club head 30 includes a face surface 32, a crown portion 33, a sole portion 34, and a side portion 35 to form a hollow structure.

The face surface 32 forms a face surface for striking a golf ball.

The crown portion 33 is connected to the face surface 32.

The sole portion 34 is connected to the face surface 32 and the crown portion 33.

The side portion 35 is connected to the crown portion 33 and the sole portion 34 and faces the face surface 32.

The golf club head 30 is made of metal, for example, and a type of metal having high strength and low specific gravitational force, such as a titanium alloy or an aluminum alloy, is preferably used.

The crown portion 33 is provided with a hosel 38 connecting to a shaft 39 at a position close to the face surface 32 and near a heel 36.

When the face surface 32 is viewed from the front, a toe 37 is on the opposite side of the heel 36 of the golf club head 30.

Method for Calculating CT Value

Next, a method for calculating the CT value and the representative CT value will be described.

The CT value of the golf club head 30 is measured such that an impactor such as an impact hammer is caused to strike the face surface 32 of the golf club head (object to be impacted), and the acceleration occurring in the impactor at this time is measured. While a configuration of the rigidity characteristic value measuring device used for measuring the CT value is described later, an acceleration sensor is attached to the impactor, and a detected value of the acceleration sensor is read into a computer.

Figure 15:
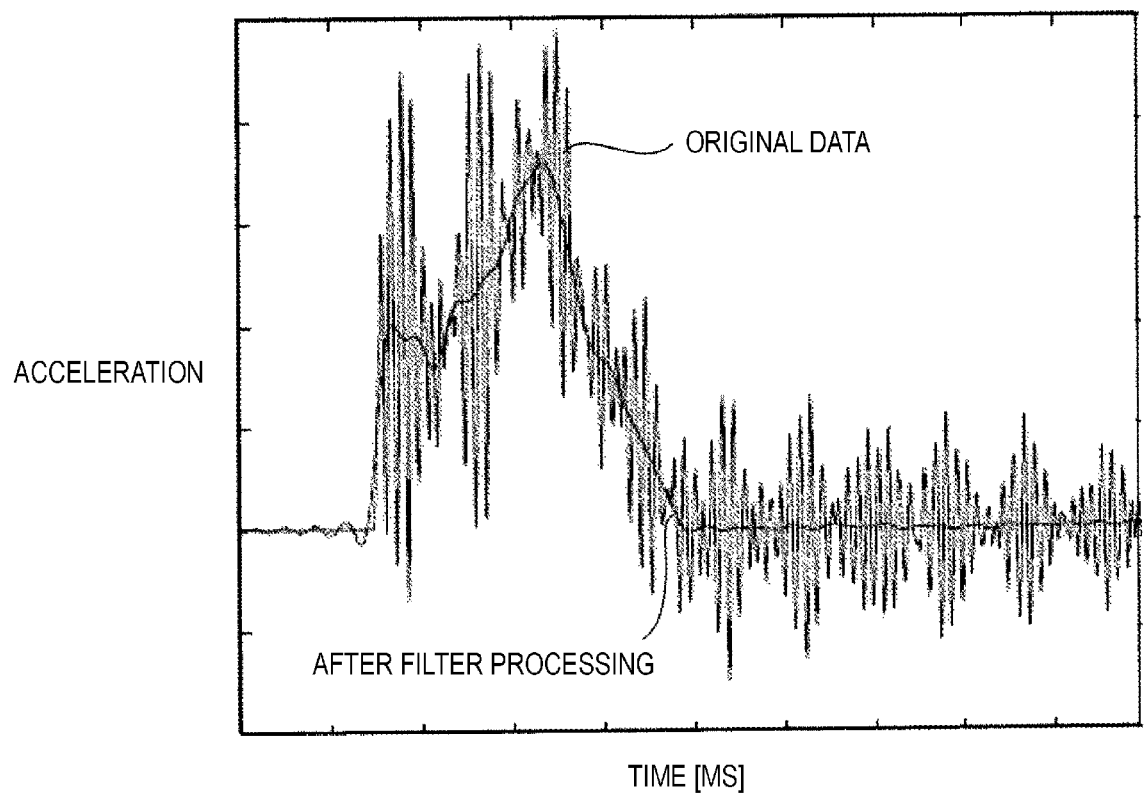
FIG. 15 is an example of acceleration data output from an acceleration sensor.

FIG. 15 is an example of acceleration data output from the acceleration sensor.

The acceleration data detected by the acceleration sensor is time series data detected at a predetermined sampling interval. As illustrated in FIG. 15, original data has large noise, and thus is smoothed by computer filtering.

Figure 16:
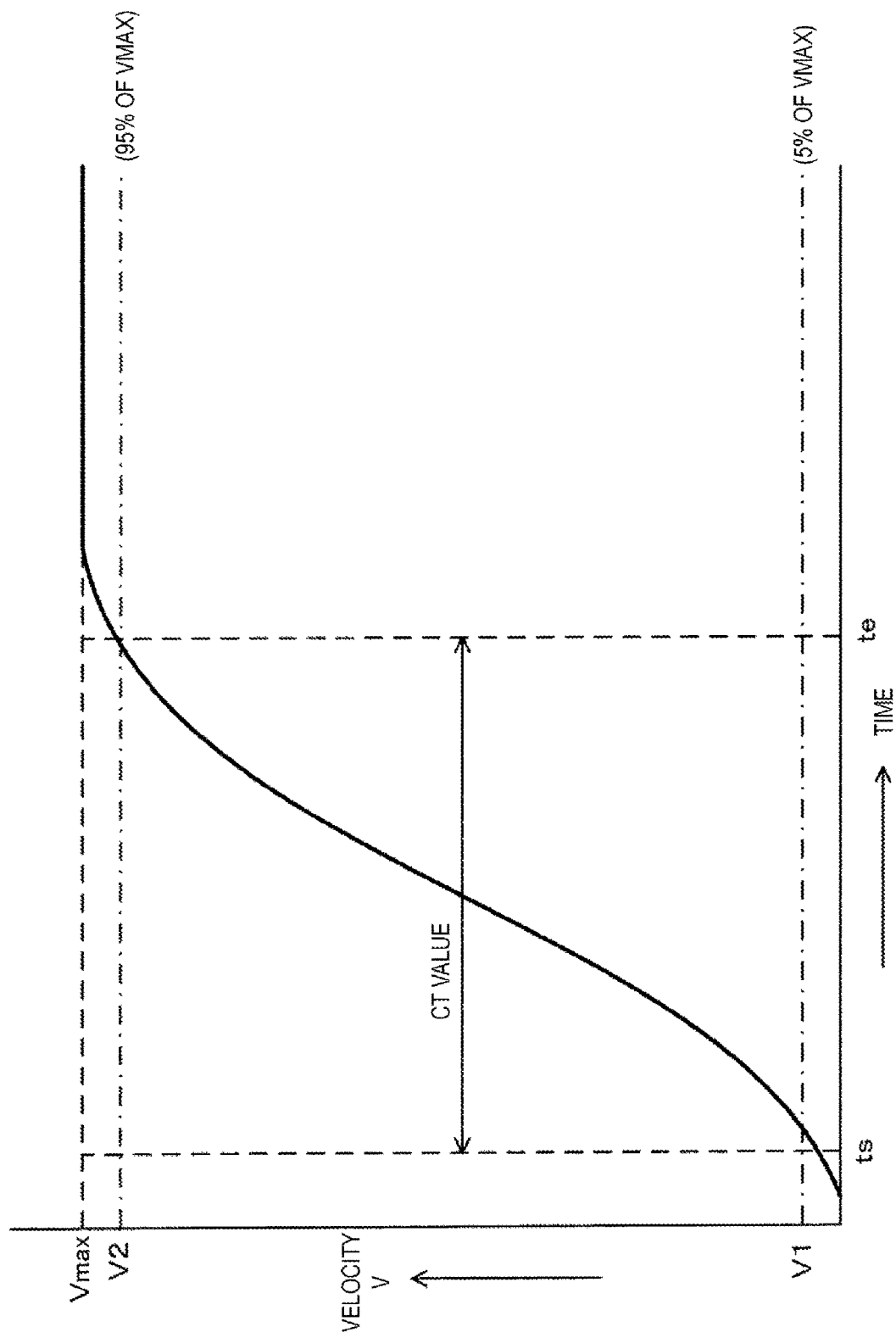
FIG. 16 is a graph showing time series data on velocity V.

The acceleration data is then integrated and converted into time series data of velocity V as shown in FIG. 16.

FIG. 16 is a graph showing the time series data on velocity V.

As described below, a computer calculates a CT value indicating rigidity characteristics of the golf club head 30.

A maximum velocity in the time series data on velocity V is denoted as Vmax.

A time at which the velocity V reaches V1 (V1=α% of Vmax) is denoted as start time ts.

A time at which the velocity V reaches V2 (V2=β% of Vmax) is denoted as end time te.

Then, α is from 0 to 99%, β is from 1 to 100%, and a is less than β.

The CT value is determined as follows: te−ts.

Typically, α is set to 5%, and β is set to 95%.

This measurement is performed multiple times while changing the impact velocity. For example, three measurements are performed every three velocity levels. Here, the velocity level is a velocity range including an upper limit velocity and a lower limit velocity. As described below, the rigidity characteristic value measuring device uses gravitational force to move the impactor, so it is difficult to exactly perform the measurement at an identical velocity. Thus, a velocity range having a predetermined width is set by having a predetermined test velocity as the center, and the measurement is performed in this range.

Figure 17:
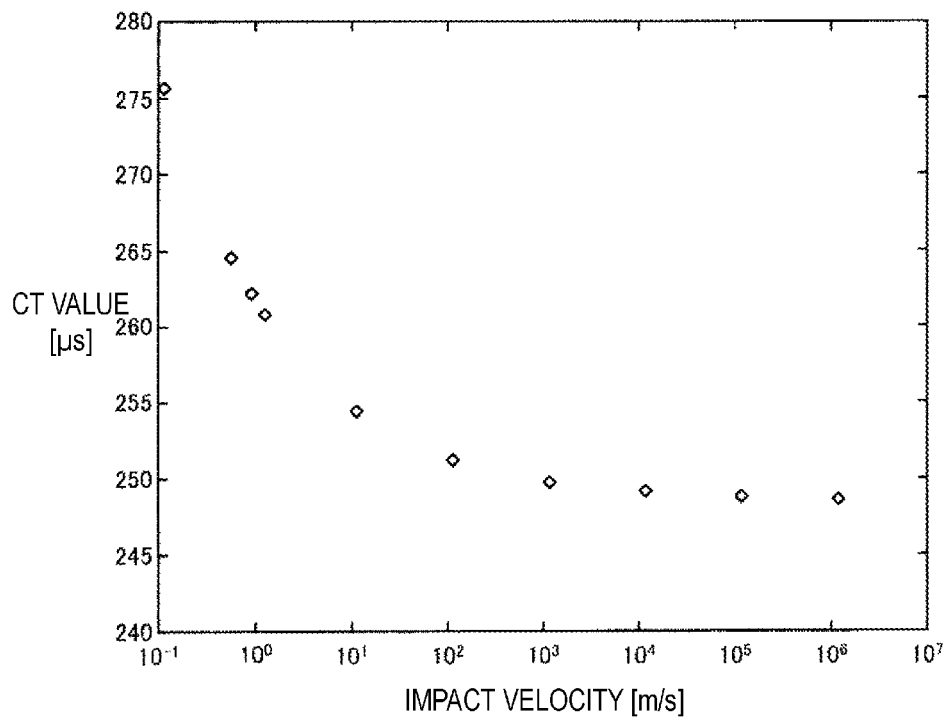
FIG. 17 is a graph showing an example of CT values measured multiple times by changing an impact velocity.

FIG. 17 is a graph showing an example of CT values measured multiple times by changing an impact velocity for the identical golf club head 30.

In FIG. 17, the horizontal axis indicates an impact velocity (m/s), and the vertical axis indicates CT values (μs).

As illustrated in the graph of FIG. 17, the CT value increases as the impact velocity decreases, and the CT value decreases as the impact velocity increases.

Figure 18:
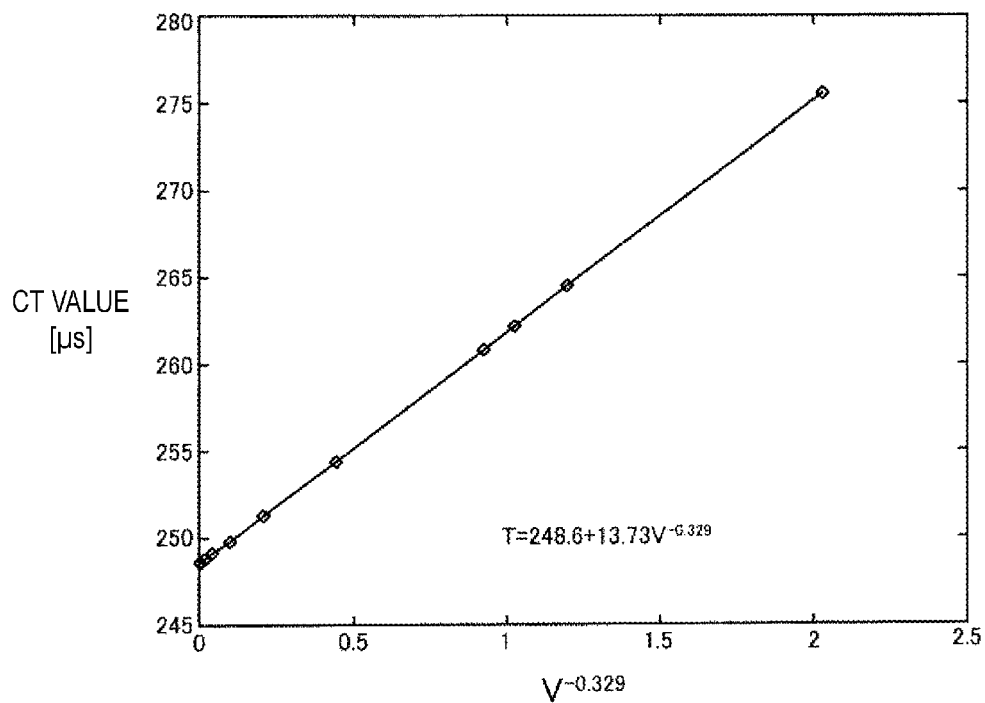
FIG. 18 is a graph obtained by converting FIG. 17.

FIG. 18 is a graph obtained by converting FIG. 17 such that a value in the horizontal axis is a value in FIG. 17 to the power of −0.329 ($V^{-0.329}$).

The conversion described above causes the CT values to align in a straight line. An intersection point (y-intercept) of the straight line and Y-axis is indicated as a representative CT value of the golf club head 30. In the example of FIG. 18, the CT value at each impact velocity is aligned on a line defined as follows: $T=248.6+13.73\ V^{-0.329}$ and a representative CT value is 248.6.

Configuration of System for Measuring Rigidity Characteristics

Next, a system for measuring the rigidity characteristics according to an embodiment will be described.

Figure 1:
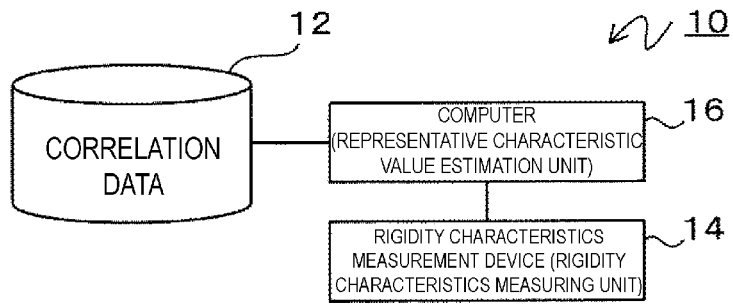
FIG. 1 is a block diagram illustrating a configuration of a system 10 for measuring the rigidity characteristics.

FIG. 1 is a block diagram illustrating a configuration of a system 10 for measuring the rigidity characteristics according to an embodiment.

The system 10 for measuring the rigidity characteristics includes correlation data 12, a rigidity characteristic value measuring device (rigidity characteristics measuring unit) 14, and a computer 16 (a representative characteristic value estimation unit) and measures a rigidity characteristic value (CT value) of the golf club head 30 based on an acceleration occurring in an impactor when the impactor is caused to strike the golf club head 30 (object to be impacted).

The correlation data 12 is calculated by measuring a representative CT value of the golf club head 30, which is calculated based on CT values measured multiple times by changing the impact velocity of the impactor, and a test velocity CT value, which is a CT value when the impact velocity is set to a predetermined test velocity, for each of the plurality of the golf club heads 30 of an identical model (a plurality of objects to be impacted belonging to a group of objects to be impacted that are each predicted to have a substantially identical velocity dependence of a CT value). The correlation data 12 is specifically data such as that shown in FIG. 6.

The correlation data is generated for each model of the golf club head 30. In addition, even in an identical model, when measured positions of CT values (impact positions of the impactor) are different, the CT values obtained are different, and thus correlation data is generated separately for each measured position. In other words, the correlation data 12 is generated for each measurement position defined for each model (each reference impact position).

Figure 10:
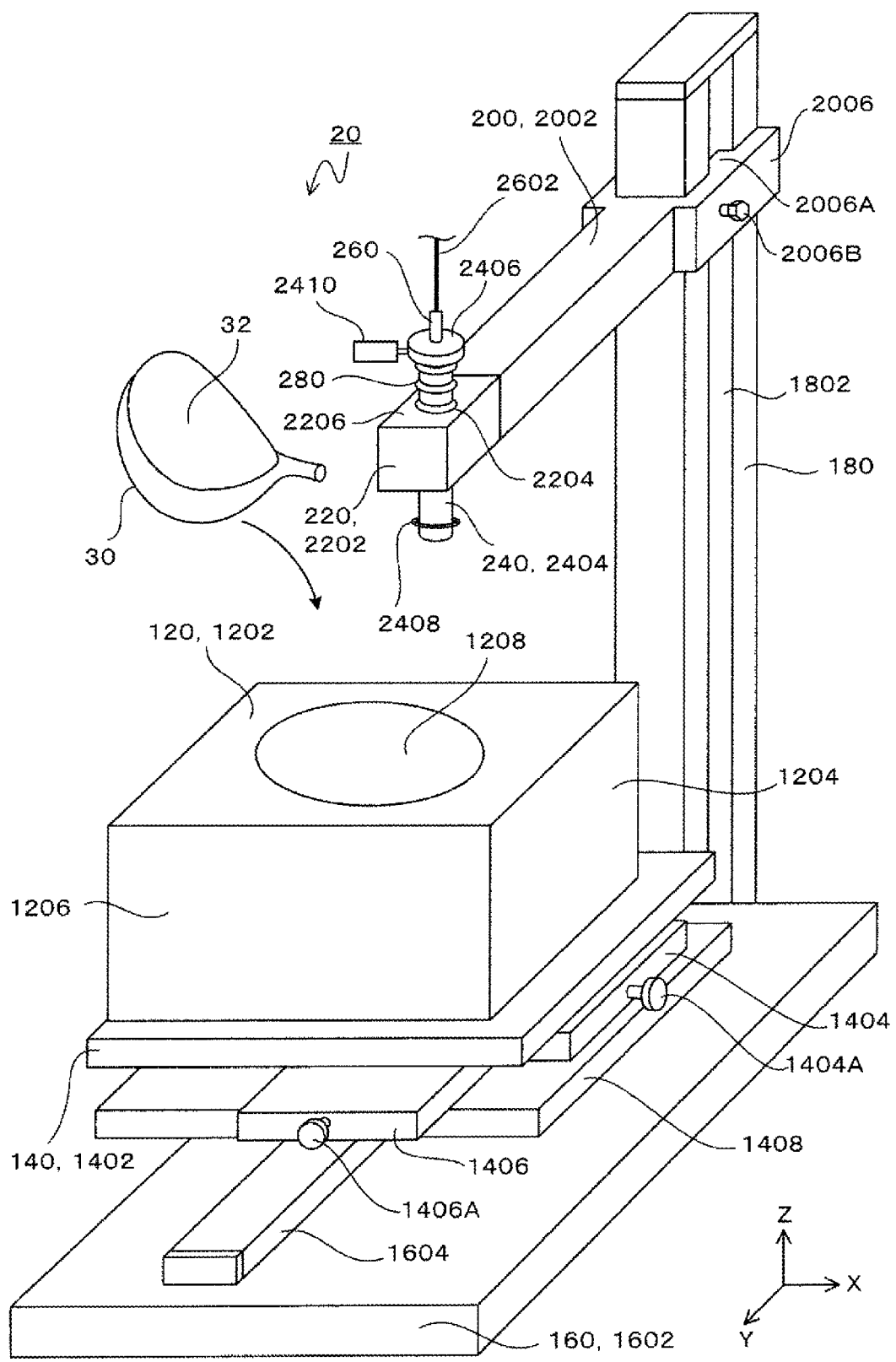
FIG. 10 is an explanatory diagram illustrating a configuration of a rigidity characteristic value measuring device 20 of a second type.

The rigidity characteristic value measuring device 14 is configured to measure a CT value and, in the present embodiment, is a device as illustrated in FIG. 10, for example. As the rigidity characteristic value measuring device 14, a known device such as that described in U.S. Pat. No. 6,837,094 or Japan Unexamined Patent Publication No. 2004-33626 may be used, for example.

In the present embodiment, a CT value at an impact velocity of a test velocity (test velocity CT value) is measured for the golf club head 30 to be measured (another object to be impacted, belonging to the group of objects to be impacted) using the rigidity characteristic value measuring device 14.

The computer 16 is configured to process data (acceleration data) obtained by measurement with the rigidity characteristic value measuring device 14 and estimates a representative CT value of the golf club head 30 to be measured (another object to be impacted) based on the test velocity CT value measured by the rigidity characteristic value measuring device 14 and the correlation data 12.

Figure 19:
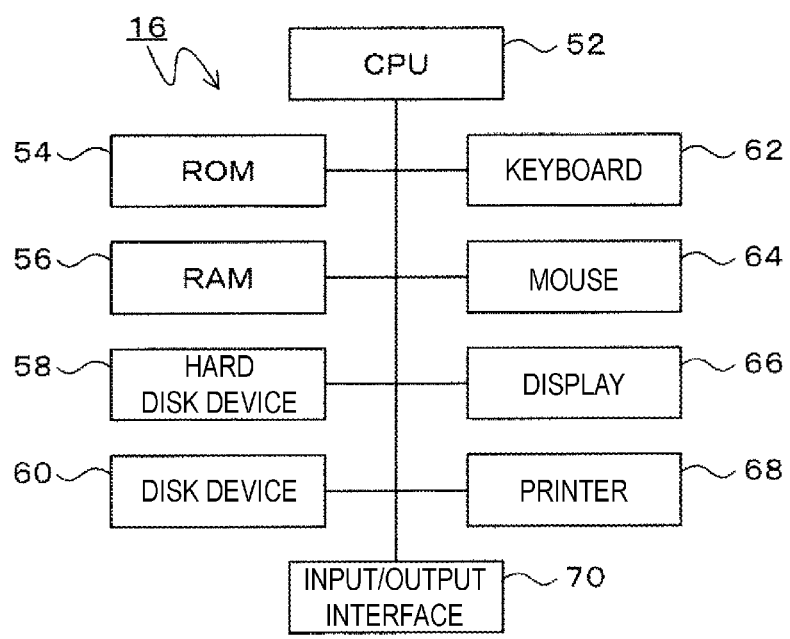
FIG. 19 is a block diagram illustrating a configuration of the computer 16.

FIG. 19 is a block diagram illustrating a configuration of the computer 16.

The computer 16 includes a CPU (Central Processing Unit) 52; and a ROM (Read Only Memory) 54, a RAM (Random Access Memory) 56, a hard disk device 58, a disk device 60, a keyboard 62, a mouse 64, a display 66, a printer 68, an input/output interface 70, and the like, connected via an interface circuit and a bus line, which are not illustrated.

The ROM 54 stores a control program, and the RAM 56 provides a working area.

The hard disk device 58 stores a CT value calculation program that calculates rigidity characteristics (CT values in the present embodiment) of the golf club head 30 (object to be impacted) based on a detection value of the acceleration sensor.

The disk device 60 records and/or plays data on a recording medium such as a CD (Compact Disc) or a DVD (Digital Video Disc).

The keyboard 62 and the mouse 64 accept input via operations by an operator.

The display 66 displays and outputs data, the printer 68 prints data and outputs data, and thus data is output using the display 66 and the printer 68.

The input/output interface 70 transmits data to and receives data from an external device, such as the rigidity characteristic value measuring device 14.

The correlation data 12 may be stored in the hard disk device 58 in the computer 16 or may be read via a network from a storage device located at another location, for example.

Next, processing in the system 10 for measuring the rigidity characteristics will be described.

Figure 2:
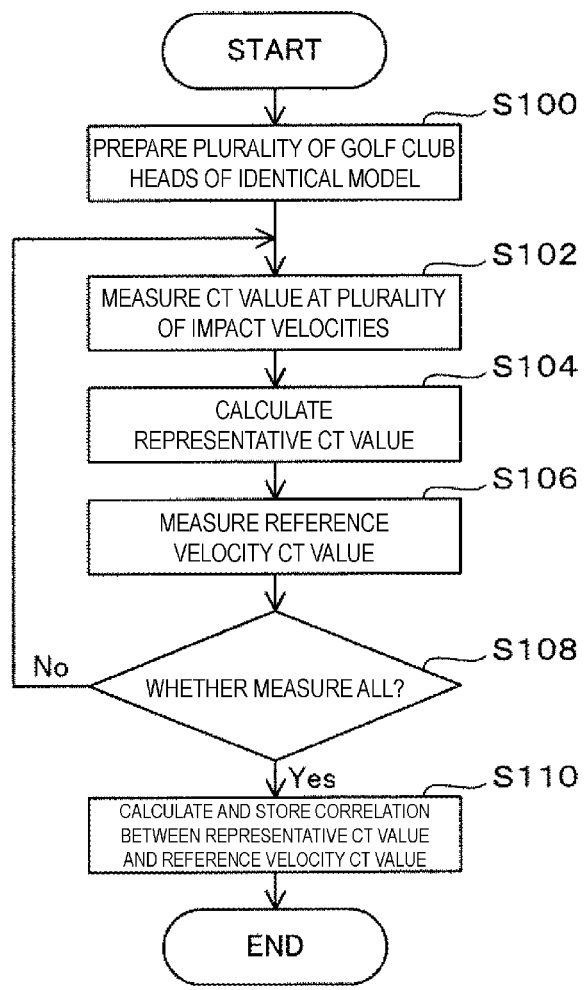
FIG. 2 is a flowchart illustrating a procedure of a method for measuring the rigidity characteristics.
Figure 3:
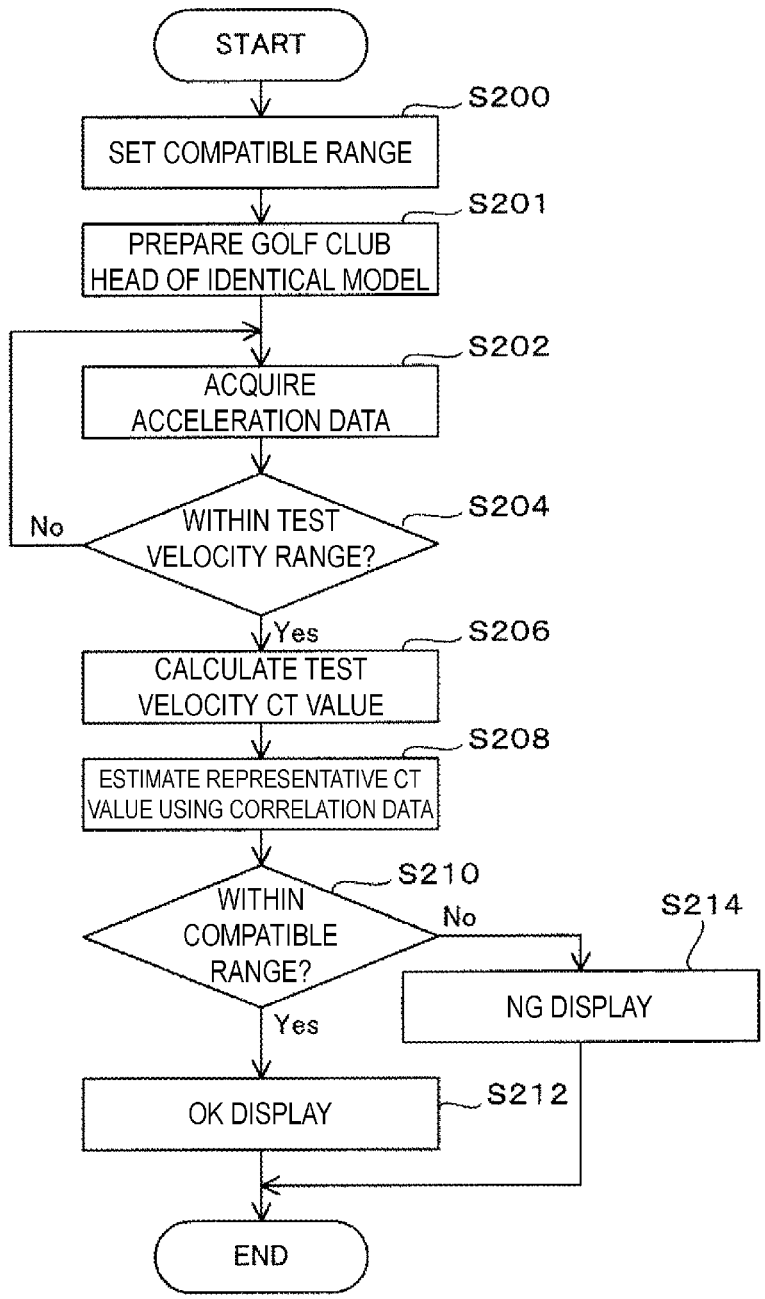
FIG. 3 is a flowchart illustrating a procedure of a method for measuring the rigidity characteristics.

FIGS. 2 and 3 are each a flowchart illustrating a procedure of a method for measuring the rigidity characteristics according to an embodiment.

The method for measuring the rigidity characteristics described below is broadly divided into the steps of: 1) calculating a correlation between a representative CT value and a test velocity CT value in advance; and 2) measuring a CT value at the test velocity and estimating a representative CT value using the correlation.

Method for Calculating Correlation Data

Referring to FIG. 2, the step 1) of calculating a correlation between a representative characteristic value and a test velocity characteristic value in advance will be described.

The processing in FIG. 2 is not necessarily required to be performed by the system 10 for measuring the rigidity characteristics illustrated in FIG. 1, and a correlation calculated using another computer or the like, for example, may be distributed as the correlation data 12.

First, the plurality of golf club heads 30 of an identical model are prepared (step S100). The golf club heads 30 of the identical model are a group of objects to be impacted that are each predicted to have a substantially identical velocity dependence of the rigidity characteristic value (CT value), and the plurality of golf club heads 30 are a plurality of objects to be impacted, belonging to the group of objects to be impacted described above.

While the number of golf club heads 30 to be prepared is freely selected, about ten to a few tens of the golf club heads 30, for example, are preferably prepared to improve the accuracy of the correlation described below.

In addition, a measuring position on the face surface 32 of the golf club head 30 is preliminarily determined. The measuring position is preferably set to a point at which the CT value is predicted to be high, for example, in terms of the structure of the golf club head 30.

The face surface 32 of the golf club head 30 has a structure of varying thickness inside the face surface 32, and the CT value varies by position. On the other hand, a golf club for competitive use has a representative CT value whose upper limit value is determined by regulations, and the representative CT value is required to be equal to or less than the upper limit value throughout the face surface 32. Thus, the measuring position (management point) is preferably set to a position at which the CT value is predicted to be high, and it is desirable to evaluate whether the CT value exceeds the upper limit value.

A plurality of measurement positions may be set for the golf club head 30 of one model; in this case, correlation data corresponding to each measuring position is generated.

Next, for one of the plurality of golf club heads 30, CT values are measured multiple times by changing the impact velocity of the impactor (step S102). In the present embodiment, three measurements were performed for each of three velocity levels. As described above, the velocity level is a velocity range having an upper limit velocity and a lower limit velocity. For example, a high velocity level VH is determined as: $\alpha$ km/s±$\beta$ km/s, and a medium velocity level VM is determined as: $\gamma$ ($<\alpha$) km/s±$\delta$ km/s.

Then, the representative CT value for the golf club head 30 is calculated based on the CT values measured in step S102 (step S104).

In other words, steps S102 and S104 correspond to the step 1) of calculating a representative characteristic value (representative CT value), which is a representative value of rigidity characteristic values of an object to be impacted (golf club head 30) based on rigidity characteristic values (CT values) measured multiple times by changing the impact velocity of the impactor.

FIG. 4 shows examples of graphs showing measurement results of a CT value of the golf club head 30.

FIG. 4 shows CT values for a total of 10 of the golf club heads 30 from No. 1 to No. 10. The vertical axis of each graph in FIG. 4 indicates a CT value, and the horizontal axis indicates a value that is an impact velocity V to the power of $-0.329$ ($V^{-0.329}$).

As shown in the No. 1 graph, measurements are performed three times for each of three velocity levels (VH, VM, and VL in order from a high-velocity side), and CT values calculated by respective measurements are analyzed by regression analysis. For example, the No. 1 graph of the golf club head 30 may be approximated as: $y=5.2529x+247.32$ (correlation coefficient $R^2=0.9921$), and the representative CT value for the golf club head 30 may be calculated as 247.32.

Figures 5, 6, 7:
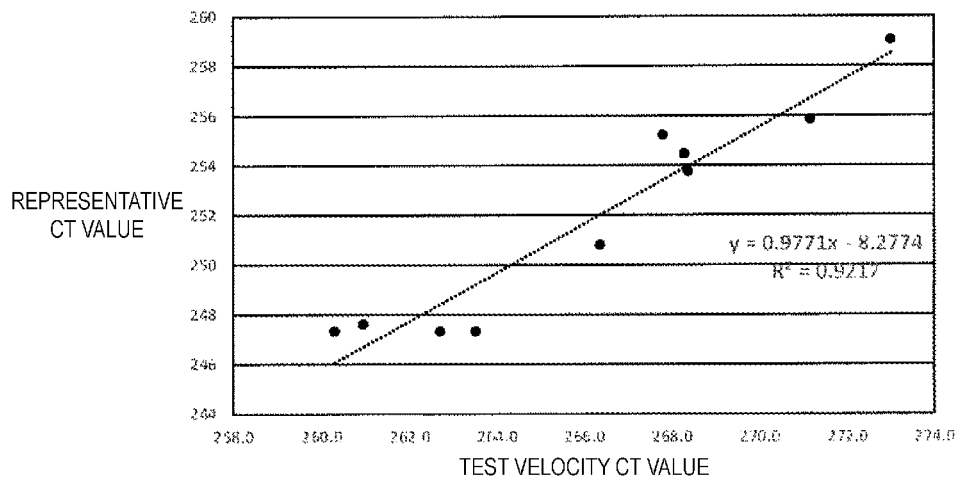
FIG. 5 is a table showing measurement results of the corresponding respective graphs of FIG. 4.
FIG. 6 is a graph showing correspondence between a representative CT value and a test velocity CT value with a regression formula.
FIG. 7 is a table showing a comparison between representative CT values calculated from a regression formula and actual representative CT values.

FIG. 5 is a table showing measurement results of the corresponding respective graphs of FIG. 4.

FIG. 5 shows representative CT values that are each rounded off to the first decimal place. In addition, the slope indicates a slope of an approximate formula, CT (VL) indicates an average value of CT values at a low velocity level VL, CT (VM) indicates an average value of CT values at the medium velocity level VM, and CT (VH) indicates an average value of CT values at the high velocity level VH.

Comparing the representative CT values of from No. 1 to No. 10, although the golf club heads 30 of an identical model have deviations, values of the "slope", each indicating velocity dependence of CT values, are within a narrow range.

Returning to the description of FIG. 1, a CT value is measured for the identical golf club head 30 at an impact velocity set to a predetermined test velocity (step S106). In other words, step S106 corresponds to the step 2) of measuring a test velocity characteristic value (test velocity CT value), which is the rigidity characteristic value (CT value) at an impact velocity set to a predetermined test velocity.

The test velocity in the present step is also set as a test velocity range having an upper limit value and a lower limit value.

While a specific numerical value of the test velocity is freely selected, the test velocity may be set to the slowest velocity range (VL in FIG. 3) of the three velocity levels measured when the representative CT value is calculated, for example. This is to avoid a flaw or the like caused in the face surface 32 due to impact by measurement when the golf club head 30 is a product to be shipped.

Here, in the present embodiment, the rigidity characteristic value measuring devices used in the step 1) and the step 2) are different in type.

Specifically, in the step 1), the rigidity characteristic value (CT value) is measured using the rigidity characteristic value measuring device of a first type, and in the step 2), the rigidity characteristic value (CT value) is measured using the rigidity characteristic value measuring device of a second type, which is different from the rigidity characteristic value measuring device of the first type.

The step 4) (refer to FIG. 3) described below is also performed using the rigidity characteristic value measuring device of the second type. In other words, the rigidity characteristic value measuring device 14 illustrated in FIG. 1 is the rigidity characteristic value measuring device of the second type.

While details of the rigidity characteristic value measuring device are described below. in the present embodiment, the rigidity characteristic value measuring device of the first type is a pendulum type device according to "Technical Description of the Pendulum Test (Revised Version)", The Royal and Ancient Golf Club of St Andrews and the United States Golf Association, November 2003, and the rigidity characteristic value measuring device of the second type is a device that vertically drops an impactor as illustrated in FIG. 10.

If the rigidity characteristic value measuring device used in the step 1) and the rigidity characteristic value measuring device used in the step 2) are each a device of an identical type (in particular, an identical device), a relational formula (refer to FIG. 17 or 18) between the impact velocity and the CT value can be calculated in a process of calculating the representative CT value. Thus, it is conceivable that the step 2) is not required to be performed.

However, when the devices used in both steps are different in type as in the present embodiment, numerical values may deviate due to differences in the measuring method. Even when the rigidity characteristic value measuring devices used in both the steps are identical in type, for example, numerical values may deviate due to an individual error in each of the devices.

Thus, the step 2) is further performed using a rigidity characteristic value measuring device that is identical in type to the rigidity characteristic value measuring device used in the step 4), and a correlation between the representative CT value obtained in the step 1) and the test velocity CT value is calculated.

Until all the golf club heads 30 prepared in step S100 are measured (No at step S108), processing returns to step S102 to repeat subsequent processes.

When all the prepared golf club heads 30 are measured (Yes at step S108), a correlation between the representative CT value and the test velocity CT value obtained for each golf club head 30 is calculated (step S110: a step of calculating a correlation).

The correlation (correlation data) calculated at this time can be acquired by applying various known techniques such as, a reference table indicating the correspondence between a representative CT value and a test velocity CT value; and a function indicating the correspondence between a representative CT value and a test velocity CT value, for example.

FIG. 6 is a graph showing correspondence between a representative CT value and a test velocity CT value with a regression formula.

The vertical axis of FIG. 6 indicates a representative CT value, and the horizontal axis thereof indicates a test velocity CT value.

The representative CT value can be approximated as: $y=0.9771x-8.2774$ (correlation coefficient $R^2=0.9217$), where the representative CT value is denoted as y and the test velocity CT value is denoted as x. That is, using the regression formula above (correlation) enables estimating the representative CT value only by measuring the test velocity CT value.

FIG. 7 is a table showing a comparison between representative CT values calculated from the regression formula of FIG. 6 and actual representative CT values. For example, when the golf club head 30 of No. 1 is reviewed, the representative CT value calculated by actual measurement is 247.3, the CT value (a converted representative CT value) obtained by substituting a test velocity CT value of 260.3 into the regression equation described above is 246.1, and thus a deviation is −1.2.

The other golf club heads 30 also have a maximum deviation of 1.9 (absolute value), so numeric values of a compatible range described below may be set in consideration of deviation in the order of the deviation above, for example.

Method for Estimating Representative CT Value Using Correlation

Next, with reference to FIG. 3, the step 2) of measuring a CT value at a test velocity and estimating a representative CT value using a correlation will be described.

Processing in FIG. 3 is performed using the system 10 for measuring the rigidity characteristics illustrated in FIG. 1.

Prior to measurement, a compatible range for the representative CT value is set (step S200). More specifically, a measurer launches a CT value measurement program of the computer 16 to set the compatible range.

In the present embodiment, for example, the upper limit value of the CT value is set to 255 µs, and the lower limit value thereof is set to 250 µs. The upper limit value is set to 255 µs in consideration of the deviation above (on the order of a maximum of 1.9) between the converted representative CT value and the actual representative CT value, with respect to an upper limit value of 257 us of a representative CT value defined by the golf regulations. In addition, while only the upper limit value is defined by the golf regulations, the lower limit value is set to secure a representative CT value that is expected as rigidity performance (rebounding performance) of golf club heads 30 of an identical model. When a significantly lower representative CT value is calculated, there may be some problem in manufacturing of the head (e.g., a wall thickness being out of a specified range).

Next, the golf club head 30 (golf club head to be measured) identical in model to the golf club head 30 used in FIG. 1 is prepared (step S201). This golf club head 30 to be measured corresponds to another object to be impacted belonging to a group of objects to be impacted that are each predicted to have a substantially identical velocity dependence of the rigidity characteristic value.

Subsequently, in the rigidity characteristic value measuring device 14, an impactor is caused to strike the face surface 32 of the golf club head 30, and acceleration data at the time of impact is measured (step S202). The acceleration data is output to the computer 16, and the computer 16 calculates the impact velocity of the impactor by integrating acceleration.

When the impact velocity is within the test velocity range (Yes at step S204), the acceleration data acquired is determined to be effective, and then the processing proceeds to step S206. On the other hand, when the impact velocity is out of the test velocity range (No at step S204), the acceleration data acquired is determined to be ineffective, and then the computer 16 performs error indication or the like. A measurer having found the error indication returns to step S202 to perform measurement again.

The computer 16 having obtained the acceleration data calculates a CT value, i.e., a test velocity CT value at the test velocity, according to the CT value measurement program (step S206). In other words, steps S202 to S206 correspond to the step 4) of measuring a rigidity characteristic value (test velocity CT value) when the impact velocity is set to the test velocity. Additionally, as illustrated in step S204, measurement is performed in the step 4) such that the impactor has an impact velocity within the test velocity range.

The test velocity CT value may be measured multiple times to improve estimation accuracy of the representative CT value. In this case, an average value of a plurality of calculated test velocity CT values is used for estimating the representative CT value.

Subsequently, the computer 16 reads out the correlation data 12 and estimates a representative CT value corresponding to the test velocity CT value calculated in step S206 (step S208). In other words, step S208 corresponds to the step 5) of estimating a representative characteristic value (representative CT value) of another object to be impacted (the golf club head 30 to be measured) based on the rigidity characteristic value (test velocity CT value) measured in the step 4) and the correlation calculated in the step 3).

The computer 16 determines whether the representative CT value estimated in step S208 is within the compatible range set in step S200 (step S210).

When it is determined to be within the compatible range (Yes at step S210), the computer 16 causes the display 66 to display an indication of being within the compatible range (OK display) (step S212).

On the other hand, when it is determined to be out of the compatible range (No at step S210), the computer 16 causes the display 66 to display an indication of being out of the compatible range (NG display) (step S214). At this time, a reason for being out of the compatible range may be displayed such that "OVER" is displayed when the representative CT value exceeds an upper limit value, and "UNDER" is displayed when the representative CT value falls short of a lower limit value, for example.

In other words, step S210 corresponds to the step 6) of determining whether the representative characteristic value (representative CT value) of the other object to be impacted (golf club head 30 to be measured), estimated in the step 5) is within the compatible range. In addition, steps S212 and S214 correspond to the step 7) of presenting a determination result in the step 6) to a measurer.

Figure 8:
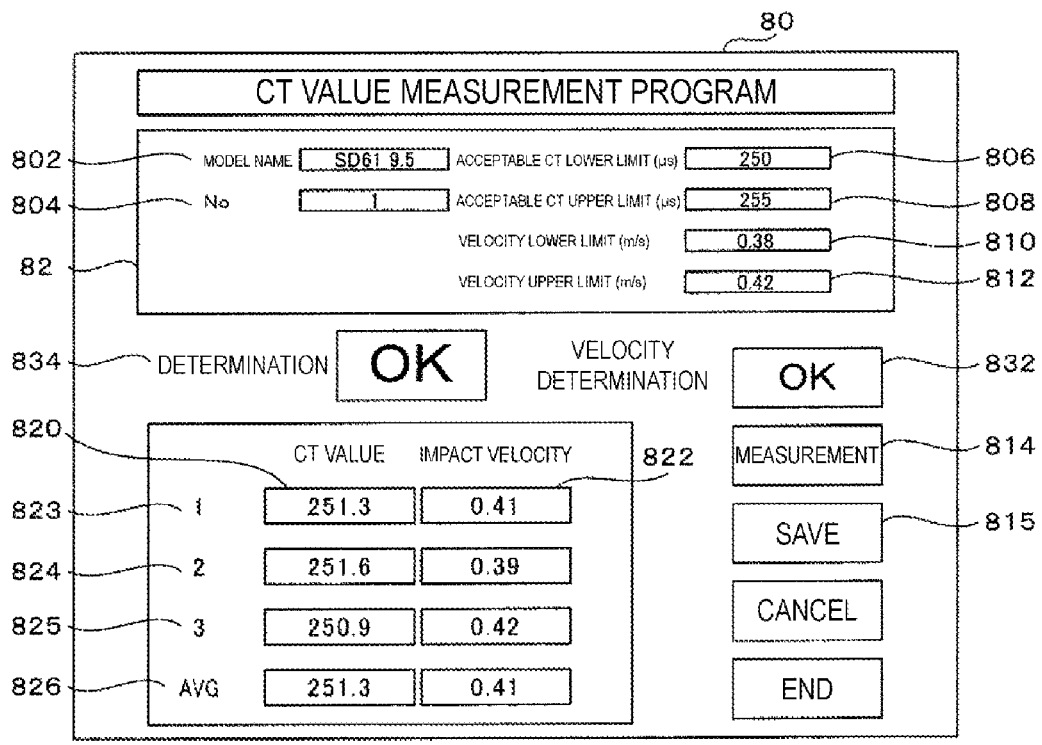
FIG. 8 is an explanatory diagram illustrating a display example of a display 66 of a computer 16.

FIG. 8 is an explanatory diagram illustrating a display example of the display 66 of the computer 16.

In FIG. 8, an interface 80 of the CT value measurement program is displayed on the display 66 (not illustrated). In the example of FIG. 8, the test velocity CT value is measured three times.

Various parameters 82 set before start of measurement are displayed on an upper row of a screen. In a model name 802, an identifier identifying a model of the golf club head 30 to be measured is input. Designating the model name 802 as appropriate enables specifying a type of correlation data used this time.

In a measuring object number 804, a serial number of each of golf club heads 30 that are to be measured by a current series of measurements.

In an acceptable CT lower limit 806, a lower limit of the compatible range described above is input.

In an acceptable CT upper limit 808, an upper limit of the compatible range described above is input.

In a velocity lower limit 810, a lower limit velocity of the test velocity range is input.

In a velocity upper limit 812, an upper limit velocity of the test velocity range is input.

Each of the values of the acceptable CT lower limit 806, the acceptable CT upper limit 808, the lower velocity limit 810, and the upper velocity limit 812 described above may be stored for each model of the golf club head 30 in association with the model name 802 above and managed together with correlation data. Specifically, at a time when the model name 802 is specified, for example, each of the values of the acceptable CT lower limit 806, the acceptable CT upper limit 808, the lower velocity limit 810, and the upper velocity limit 812 may be automatically identified and displayed on the screen.

When setting the golf club head 30 to be measured this time in the rigidity characteristic value measuring device 14 and completing the input of the various parameters 82, a measurer clicks a measuring button 814. Then, the measurer operates the rigidity characteristic value measuring device 14 to cause the impactor to strike the face surface 32 of the golf club head 30. The computer 16 receives acceleration data at the time of the impact. The computer 16 integrates the acceleration data to calculate an impact velocity.

When the impact velocity is within a range of the test velocity range, the computer 16 displays "OK" in a velocity determination column 832 and displays an impact velocity 822 and a CT value 820 in a first measurement result display column 823.

When the impact velocity is out of the range of the test velocity range, "NG" or "OVER" or "UNDER" is displayed in the velocity determination column 832. The measurer adjusts the rigidity characteristic value measuring device 14 as necessary and then presses the measuring button 814 again to perform the measurement.

The measurer repeats the measurement until three measurements are completed. The second and third measurement results are displayed in measurement result display columns 824 and 825, respectively.

When the three measurements are completed, the computer 16 displays an average value of impact velocities and an average value of CT values in an average result display column 826.

The computer 16 also determines whether the average value of the CT values measured three times is within the compatible range. The computer 16 displays "OK" in a CT value determination column 834 when the average value is within the compatible range and displays "NG" or "OVER" or "UNDER" in the CT value determination column 834 when the average value is out of the compatible range.

When the measurement is completed, the measurer clicks a save button 815 to store current measurement results.

Subsequently, the measurer changes the measuring object number 804 to set the subsequent golf club head 30 in the rigidity characteristic value measuring device 14 and repeats the above operation.

When the save button 815 is pressed, the measuring object number 804 may be automatically numbered up, i.e., a serial number corresponding to a subsequent golf club head to be measured may be automatically input.

Configuration of Rigidity Characteristic Value Measuring Device

Next, the details of a rigidity characteristic value measuring device used in the system 10 for measuring the rigidity characteristics will be described.

As described above, the present embodiment includes the step 1) (steps S102 and S104 in FIG. 2) in which CT values are measured using the rigidity characteristic value measuring device of the first type; and the step 2) (step S106 in FIG. 2) and the step 4) (steps S202 to S206 in FIG. 3) in which CT values are measured using the rigidity characteristic value measuring device of the second type.

Rigidity Characteristic Value Measuring Device of First Type

The rigidity characteristic value measuring device of the first type is a pendulum type device according to "Technical Description of the Pendulum Test (Revised Version)", The Royal and Ancient Golf Club of St Andrews and the United States Golf Association, November 2003. The rigidity characteristic value measuring device of the first type has a widely known configuration, and thus only an overview will be described in the present specification.

Figure 9:
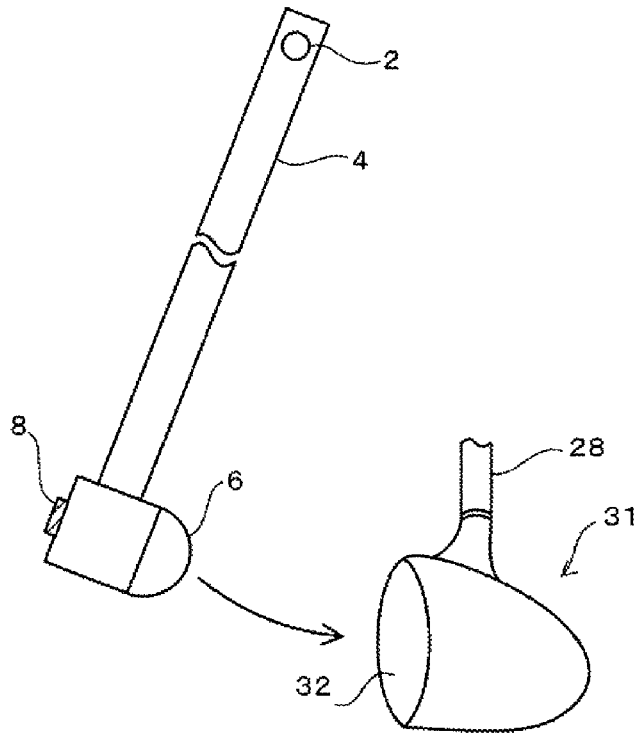
FIG. 9 is a side view illustrating a principle of a rigidity characteristic value measuring device of a first type.

FIG. 9 is a side view illustrating a principle of the rigidity characteristic value measuring device of the first type.

The measuring device includes a support shaft 2 with an axis extending horizontally, an arm 4 provided with an upper end supported on the support shaft 2, the upper end being capable of swinging, an impactor 6 formed of a hemispherical metal material, the metal material being fixed to a lower end of the arm 4, an acceleration sensor 8 attached to the impactor 6, and a chuck (not illustrated) for fixing a shaft 28 of a golf club 31.

The face surface 32 is oriented such that a moving direction of the impactor 6 when the impactor 6 strikes the face surface 32 is orthogonal to the face surface 32. The shaft 28 is fixed by the chuck to maintain this state.

A test procedure is as follows.

First, the impactor 6 is lifted until an angle formed between the arm 4 and a vertical line reaches a predetermined angle, and then the arm 4 is swung down. Adjusting the angle formed between the arm 4 and the vertical line enables adjusting the impact velocity of the impactor 6 on the face surface 32.

Accordingly, the arm 4 is swung downward with the support shaft 2 as a fulcrum, and then the impactor 6 strikes the face surface 32.

A detected value of the acceleration sensor 8 at the time of the impact is output to a computer (not illustrated). The computer calculates a CT value using the detected value of the acceleration sensor 8.

Rigidity Characteristic Value Measuring Device of Second Type

FIG. 10 is an explanatory diagram illustrating a configuration of a rigidity characteristic value measuring device 20 of a second type.

The rigidity characteristic value measuring device 20 of the second type includes a head fixing jig 120, an XY stage 140, a pedestal 160, a supporting column 180, an arm 200, a linear bushing 220, an impact rod 240, and an acceleration sensor 260.

The head fixing jig 120 functions as a holding mechanism for holding an object to be impacted with its surface to be measured facing upward. In the present embodiment, the head fixing jig 120 in a rectangular parallelepiped shape includes an upper surface 1202 facing the impact rod 240 disposed above, a lower surface (not illustrated) in contact with the XY stage 140, a side surface 1204 facing a horizontal direction (X-direction) on the page, and a side surface 1206 facing a depth direction (Y-direction) on the page.

The upper surface 1202 is formed with a fitting hole 1208 into which the golf club head 30 fits. The fitting hole 1208 is formed in the same form as that of the side portion 35 of the golf club head 30, and the golf club head 30 can be fitted thereinto with the face surface 32 (surface to be measured) facing upward. The golf club head 30 fitted into the fitting hole 1208 is held by the head fixing jig 120 with the face surface 32 facing upward. The fitting hole 1208 is formed in a shape in which at this time, the face surface 32 is substantially horizontal, i.e., a normal line at a face center is the vertical direction. When the golf club head 30 having a different model number (shape) is measured, the head fixing jig 120 is replaced with one that is formed in accordance with the shape of the golf club head 30.

The head fixing jig 120 is formed of a damping material such as silicon. This is because vibration of the golf club head 30, caused when the impact rod 240 described below strikes the face surface 32, is attenuated to reduce the measured noise in the acceleration sensor 260. In other words, the head fixing jig 120 serving as a holding mechanism is formed containing a vibration damping material that attenuates vibration of the golf club head 30 being an object to be impacted.

The XY stage 140 includes a movable table 1402, an X-axis direction adjustment unit 1404, a Y-axis direction adjustment unit 1406, and a base 1408.

The movable table 1402 is mounted with the head fixing jig 120.

The X-axis direction adjustment unit 1404 includes an X-axis direction operation mechanism and an X-axis direction movement mechanism. When a knob 1404A constituting the X-axis direction operation mechanism is rotated, the X-axis direction movement mechanism is actuated to move the movable table 1402 in the X-axis direction.

The Y-axis direction adjustment unit 1406 includes a Y-axis direction operation mechanism and a Y-axis direction movement mechanism. When a knob 1406A constituting the Y-axis direction operation mechanism is rotated, the Y-axis direction movement mechanism is actuated to move the movable table 1402 in the Y-axis direction.

The Y-axis direction adjustment unit 1406, the X-axis direction adjustment unit 1404, and the movable table 1402 are disposed on an upper surface of the base 1408. In addition, on a bottom surface of the base 1408, rail receivers (not illustrated) that fit with rails 1604 of the pedestal 160 described below are formed.

The mechanism of the XY stage 140 is not limited to the above, and various known mechanisms can be employed.

In the present embodiment, the XY stage 140 enables not only the head fixing jig 120 (the holding mechanism) to move in the horizontal direction (XY direction), but also a drop position of the impact rod 240 (impactor) to be adjusted on the face surface 32 (surface to be measured) of the golf club head 30 (object to be impacted).

The drop position of the impact rod 240 (impactor) on the face surface 32 (surface to be measured) of the golf club head 30 (object to be impacted) may be adjustable by allowing the linear bushing 220 (dropping mechanism) described below to be moved in the horizontal direction (XY direction).

The pedestal 160 includes a bottom plate portion 1602 and the rails 1604.

The bottom plate portion 1602 is disposed on a stable horizontal surface, such as a workbench.

The rails 1604 are disposed on the bottom plate portion 1602 along the Y-axis direction, and the base 1408 of the XY stage 140 is disposed on the rails 1604. The base 1408 of the XY stage 140 is movable on the rails 1604 in the depth direction (Y-axis direction) on the page.

The rails 1604 have a magnet (position fixing mechanism) that is not illustrated and attached to a terminal portion on a back side on the page (supporting column 180 side). In the present embodiment, the base 1408 of the XY stage 140 is made of metal such as stainless steel. When the base 1408 moves to the terminal portion (measuring position) on the back side of the rails 1604 on the page, the base 1408 is attracted to the magnet to cause the position of the XY stage 140 to be fixed.

The supporting column 180 is erected vertically (in the Z-axis direction) upward from an end of the bottom plate portion 1602.

The arm 200 includes an arm body 2002 and a position fixing mechanism 2006. The arm body 2002 and the position fixing mechanism 2006 are connected to each other.

The arm body 2002 extends from the supporting column 180 in the horizontal direction (Y-axis direction) toward a front surface of the device (a side on which the XY stage 140 and the like are disposed).

The position fixing mechanism 2006 includes a protrusion 2006A that fit into a groove 1802 provided in the supporting column 180; and a bolt 2006B.

The protrusion 2006A is coupled to the groove 1802 in a vertically movable manner to allow the arm body 2002 and the position fixing mechanism 2006 to move in the vertical direction (Z-axis direction) along the supporting column 180.

The bolt 2006B presses a side surface of the supporting column 180 by being rotationally operated to fix the arm body 2002 and the position fixing mechanism 2006 to the supporting column 180 in an immovable manner. Releasing the bolt 2006B from pressing the side surface of the supporting column 180 enables the arm body 2002 and the position fixing mechanism 2006 to move in the vertical direction along the supporting column 180.

The position fixing mechanism 2006 allows the arm body 2002 to move in the vertical direction and in turn allows the linear bushing 220 connected to the arm body 2002 to move in the vertical direction. This enables a distance in the vertical direction to be adjusted, between a dropping start position of the impact rod 240 (impactor) described below and the face surface 32 (surface to be impacted) of the golf club head 30 (object to be impacted). In other words, the position fixing mechanism 2006 functions as a drop-distance adjustment mechanism.

The distance in the vertical direction between the dropping start position of the impact rod 240 and the face surface 32 can be adjusted as described above, such that the impact velocity of the impact rod 240 on the face surface 32 can change according to the distance. The CT value to be measured in the present embodiment is known to be velocity dependent. Thus, the impact velocity of the impact rod 240 on the face surface 32 is predetermined, and measurement needs to be performed at the impact velocity. Providing the drop-distance adjustment mechanism enables adjusting the impact velocity of the impact rod 240 on the face surface 32 as desired.

The linear bushing 220 is attached to a leading end of the arm body 2002 of the arm 200 and functions as a dropping mechanism that causes the impact rod 240 (impactor) to drop in the vertical direction (longitudinal direction of the impact rod 240 in a columnar shape) toward the golf club head 30 (object to be impacted).

The linear bushing 220 includes a body portion 2202 and an insertion hole 2204. The insertion hole 2204 passes through a lower surface 2208 from an upper surface 2206 of the body portion 2202 (refer to FIG. 12). Steel balls are disposed in an inner circumferential surface of the insertion holes 2204 in the body portion 2202 to guide the impact rod 240 inserted into the insertion hole 2204 vertically downward.

Using the linear bushing 220 regulates a drop direction of the impact rod 240, so a drop position on the golf club head 30 can be adjusted with high accuracy.

Figure 11:
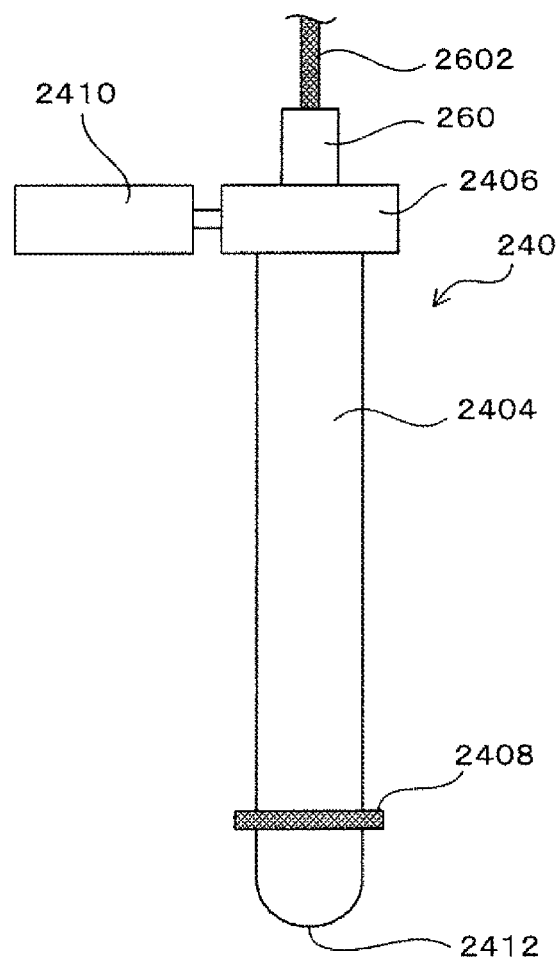
FIG. 11 is an enlarged view of an impact rod 240.

As illustrated in FIG. 11, the impact rod 240 (impactor) includes a rod body 2404, an upper stopper 2406, a lower stopper 2408, and an operating lever 2410.

The rod body 2404 is a cylindrical rod-like member and is made of metal such as stainless steel. The rod body 2404 may have a column shape other than a cylindrical column (e.g., a prism shape or the like). The rod body 2404 has a bottom surface 2412 (bottom surface on a side striking the golf club head 30 (object to be impacted) in a use state) that is formed in a spherical shape. The rod body 2404 is formed having a diameter that allows the rod body 2404 to drop out of the insertion hole 2204 of the linear bushing 220.

The upper stopper 2406 is attached to an upper end portion (end portion opposite the bottom surface 2412) of the rod body 2404. The upper stopper 2406 has an outer diameter greater than an inner diameter of the insertion hole 2204 of the linear bushing 220, so that the upper stopper 2406 cannot go through the insertion hole 2204 of the linear bushing 220. Thus, when the impact rod 240 is dropped, the impact rod 240 cannot move downward from a position where the upper stopper 2406 comes into contact with the upper surface 2206 of the linear bushing 220. In other words, the upper stopper 2406 regulates a lowermost position of the impact rod 240 positioned in the insertion hole 2204 of the linear bushing 220.

In actual use, as illustrated in FIGS. 10 and 12, a spring 280 is interposed between the upper stopper 2406 and the upper surface 2206 of the linear bushing 220, such that the upper stopper 2406 and the upper surface 2206 do not directly come into contact with each other. The spring 280 is a compression coil spring, for example, and the rod body 2404 of the impact rod 240 is inserted into an inner diameter side of the spring 280.

As described in detail below, the spring 280 functions as a re-impact preventing mechanism that holds the impact rod 240 above the face surface 32 after the impact rod 240 (impactor) strikes the face surface 32 (surface to be measured), preventing the impact rod 240 (impactor) from re-striking the face surface 32 (surface to be measured).

The lower stopper 2408 is attached close to the bottom surface 2412 of the rod body 2404.

The lower stopper 2408 is formed of a flexible member and is made of rubber, for example.

The lower stopper 2408 has an outer diameter greater than the inner diameter of the insertion hole 2204 of the linear bushing 220, such that the lower stopper 2408 also cannot go through the insertion hole 2204 of the linear bushing 220. Thus, when the impact rod 240 is moved upward, the impact rod 240 cannot move upward from a position where the lower stopper 2408 comes into contact with the lower surface 2208 of the linear bushing 220. In other words, the lower stopper 2408 regulates an uppermost position of the impact rod 240 positioned in the insertion hole 2204.

In addition, the lower stopper 2408 is detachable from the rod body 2404. To remove the impact rod 240 from the linear bushing 220, the lower stopper 2408 is removed from the rod body 2404, and then the rod body 2404 is moved upward to be pulled out from the insertion hole 2204. Then, to attach the impact rod 240 to the linear bushing 220, the rod body 2404 having the lower stopper 2408 removed is inserted into the insertion hole 2204, and then the rod body 2404 is moved downward to a position regulated by the spring 280. After that, the lower stopper 2408 is attached to the rod body 2404.

In other words, as described above, the linear bushing 220 (dropping mechanism) holds the impact rod 240 (impactor) in a vertically movable manner, and the upper stopper 2406 and the lower stopper 2408 each function as a stopper mechanism for regulating the uppermost position and the lowermost position of the impact rod 240 inserted (held) in the linear bushing 220.

The operating lever 2410 is a rod-like member attached to the upper stopper 2406 and is used by a measurer to move the impact rod 240 to an upward position (refer to FIG. 12). More specifically, after holding the operating lever 2410 to lift the impact rod 240 upward, a measurer releases the operating lever 2410 to allow the impact rod 240 to free fall.

The impact rod 240 preferably has a size such as the rod body 2404 having a diameter of 12 mm or more and 20 mm or less; and a length (length from a boundary between the upper stopper 2406 and the acceleration sensor 260 to the bottom surface 2412) of 60 mm or more and 120 mm or less and preferably also has a mass (including the rod body 2404, the upper stopper 2406, the lower stopper 2408, and the operating lever 2410) of 100 g or more and 200 g or less; and a radius of curvature of the bottom surface 2412 of 20 mm or more and 30 mm or less.

This is because the impactor defined in the pendulum impact test procedure (refer to "Technical Description of the Pendulum Test (Revised Version)", The Royal and Ancient Golf Club of St Andrews and the United States Golf Association, November 2003) has a size within the range described above.

The acceleration sensor 260 is attached to a surface of the impact rod 240 (impactor), opposite the bottom surface 2412, to measure the acceleration of the impact rod 240, which is caused when the impact rod 240 strikes the face surface 32 (object to be impacted).

The acceleration sensor 260 is connected to a computer (not illustrated) using a wire 2602 and outputs a detected value to the computer. The acceleration sensor 260 and the computer may be connected via wireless communication.

Figure 13:
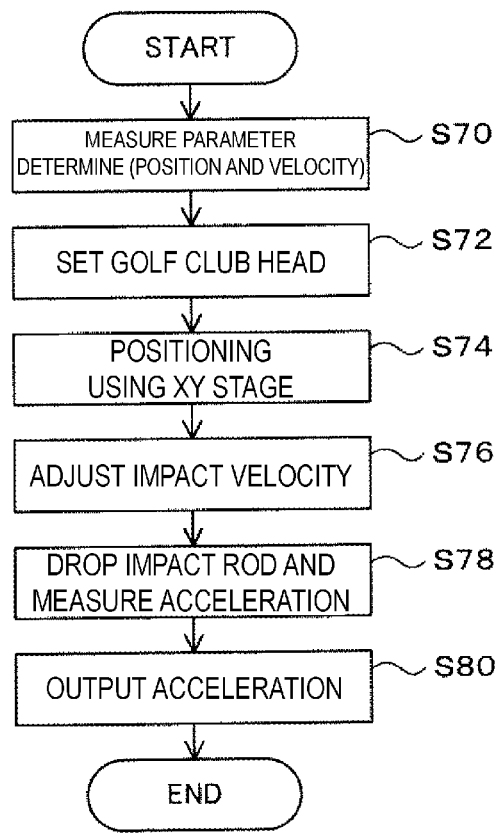
FIG. 13 is a flowchart illustrating a measurement procedure of the rigidity characteristic value measuring device 20 of the second type.

Next, with reference to the flowchart of FIG. 13, a measurement procedure using the rigidity characteristic value measuring device 20 of the second type will be described.

Prior to measurement, measurement parameters such as a measurement position of rigidity characteristics (impact position of the impact rod 240 on the face surface 32) and an impact velocity of the impact rod 240 are determined (step S70).

Next, the golf club head 30 is set in the head fixing jig 120 (step S72).

More specifically, a measurer first causes the XY stage 140 on the rails 1604 to move in a forward direction. This is to move the head fixing jig 120 to a position where it does not interfere with the linear bushing 220 and the like when the golf club head 30 is set. Subsequently, with the face surface 32 of the golf club head 30 facing upward, the side portion 35 thereof is fitted into the fitting hole 1208. Then, the XY stage 140 on the rails 1604 is moved in the back direction (toward the supporting column 180). When the XY stage 140 moves back to an end portion of each of the rails 1604, the magnet fixes the XY stage 140 to the position thereof.

Subsequently, the XY stage is operated to align a measurement position on the face surface 32 and a drop position of the impact rod 240 such that the positions coincide with each other (step S74).

In addition, a position of the arm 200 with respect to the support column 180 is adjusted to adjust the impact velocity of the impact rod 240 on the face surface 32 (step S76). In other words, when the impact rod 240 free falls toward the face surface 32, its impact velocity varies in accordance with a dropping start position of the impact rod 240. Thus, for example, the acceleration is measured by actually causing the impact rod 24 to strike the face surface 32. Then, the acceleration is integrated to calculate the impact velocity. When the impact velocity is more than the impact velocity determined in step S70, a position of the arm 200 is adjusted to be raised. When the impact velocity is less than that, the position of the arm 200 is adjusted to be lowered.

As described below (refer to FIG. 12), the impact rod 240 strikes the face surface 32, compressing the spring 280. When the position of the arm 200 is raised and a distance between the dropping start point of the impact rod 240 and the face surface 32 is increased, the spring 280 is greatly compressed at the time of impact, and the impact rod 240 decreases in impact velocity compared to a previous position change of the arm 200. When the position of the arm 200 is raised excessively, the impact rod 240 and the face surface 32 do not come into contact with each other.

In addition, when the position of the arm 200 is lowered and the distance between the dropping start point of the impact rod 240 and the face surface 32 is shortened, the impact rod 240 strikes the face surface 32 with a small amount of compression of the spring 280 (before deceleration). This causes the impact rod 240 to increase in impact velocity compared to a previous position change of the arm 200. When the position of the arm 200 is lowered excessively, the impact rod 240 and the face surface 32 come into contact with each other even when unloaded.

Subsequently, the impact rod 240 is caused to drop onto the face surface 32, and acceleration at the time of impact is measured by the acceleration sensor 260 (step S78). Then, the detected value of the acceleration sensor 260 is output to the computer (step S80), and the processing of the flowchart ends.

FIG. 12 is a diagram schematically illustrating the behavior of the impact rod 240 during measurement.

Figure 12A:
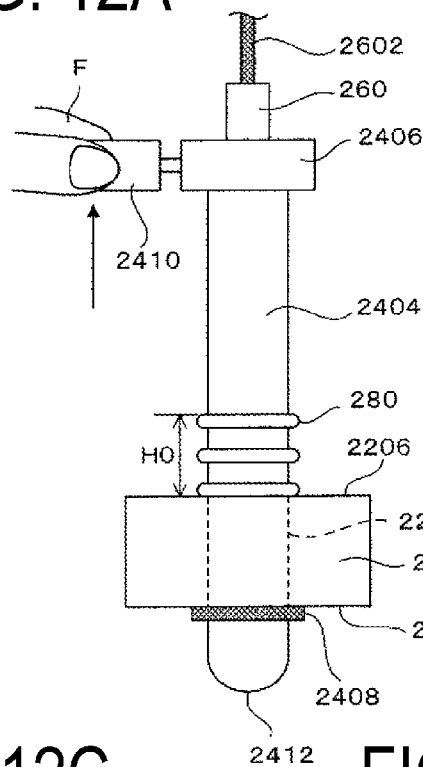
FIG. 12 is a diagram schematically illustrating the behavior of the impact rod 240 during measurement.

First at the time of measurement, as illustrated in FIG. 12A, a measurer holds the operating lever 2410 and pulls upward the impact rod 240. When the impact rod 240 is pulled up by a predetermined amount, the lower stopper 2408 comes into contact with the lower surface 2208 of the linear bushing 220, and then the impact rod 240 cannot further move upward.

During the measurement, the spring 280 is inserted onto the rod body 2404 of the impact rod 240. The spring 280 is positioned on the upper surface 2206 of the linear bushing 220. In the state of FIG. 12A, the spring 280 is not subject to force, so that the spring 280 has a natural length H0.

Figure 12B:
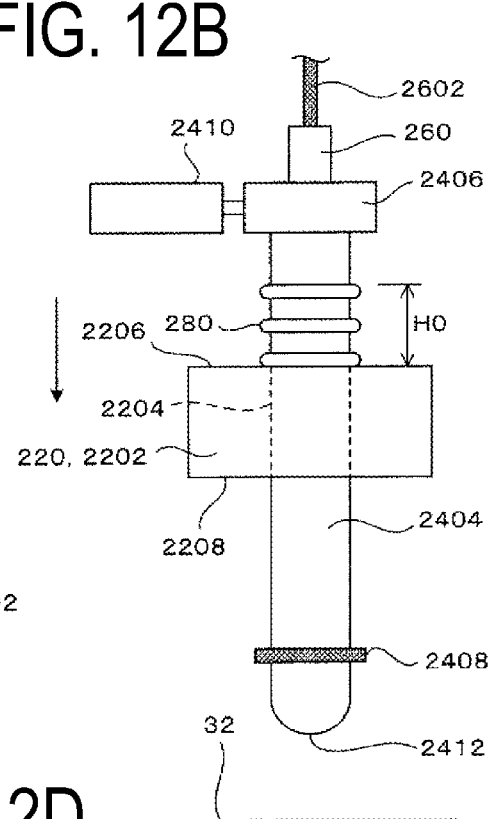
Figure 12C:
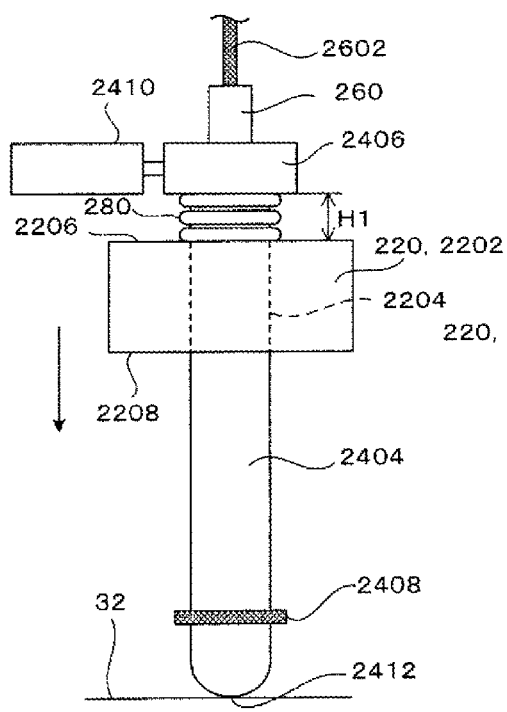

Subsequently, turning on the acceleration sensor 260 (measurement start), the measurer releases the operating lever 2410 to cause the impact rod 240 to drop in the vertical direction. As illustrated in FIG. 12B, the impact rod 240 free falls, and the falling velocity is accelerated by gravitational acceleration.

After that, when the upper stopper 2406 drops to an upper end position of the spring 280, a load (mass x acceleration) of the impact rod 240 is applied to the spring 280. This load causes the spring 280 to contract to a length H1 that is shorter than the natural length H0 (refer to FIG. 12C). Then, a reaction force from the spring 280 is applied to the impact rod 240, and the falling velocity is reduced. During this deceleration, the impact rod 240 strikes the face surface 32 at a predetermined impact velocity.

The impact rod 240 having impacted on the face surface 32 moves upward due to a reaction force received. When the impact rod 240 moves upward, no load is applied to the spring 280, and then the spring 280 returns to the natural length H0. After moving upward by a certain distance, the impact rod 240 falls downward (toward the face surface 32) again due to gravitational force. However, the dropping start position is lower than that of the initial drop, so the load applied to the spring 280 decreases, and thus the load to the spring 280 does not reach the level that causes the spring 280 to contract (or the amount of contraction decreases compared to FIG. 12C).

Figure 12D:
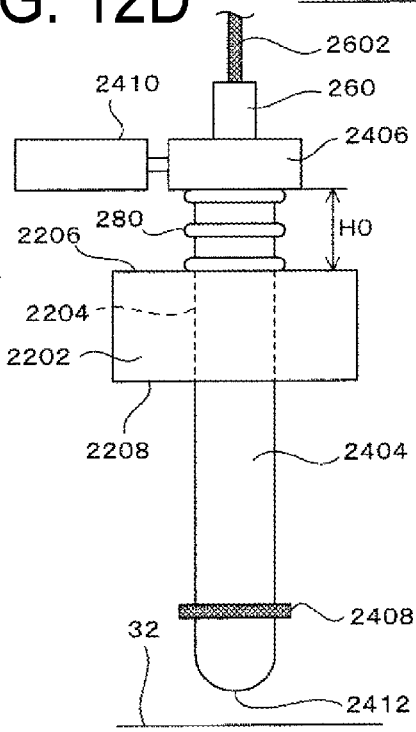

Accordingly, as illustrated in FIG. 12D, the bottom surface 2412 of the impact rod 240 is held above the face surface 32. In other words, the spring 280 functions as the re-impact preventing mechanism that holds the impact rod 240 above the face surface 32, preventing the impact rod 240 from re-striking the face surface 32 after the impact rod 240 (impactor) strikes the face surface 32 (surface to be measured).

The re-impact preventing mechanism described above is provided to prevent noise in a detected value of the acceleration sensor 260 from increasing due to a re-impact.

As described above, the rigidity characteristic value measuring device 20 of the second type causes the impact rod 240, an impactor, to fall vertically toward the golf club head 30, an object to be impacted. This facilitates maintaining an impact position and an impact angle of the impact rod 240 in a constant manner and has an advantage of improving the measurement accuracy of the rigidity characteristics.

In particular, the rigidity characteristic value measuring device of the first type (refer to FIG. 9) is configured based on the premise that a test is performed in a club shape in which a head and a shaft are integrated, so the test needs to be performed by holding a shaft portion. This causes a problem in that a step of attaching a shaft is required to perform measurement for quality control in a manufacturing process of a head, for example, and the step is cumbersome.

The shaft has a cylindrical shape, and thus is liable to rotate in its circumferential direction. This makes it difficult to set an impact angle with the impactor to be maintained in a constant manner during the test. In addition, rigidity characteristics may change due to the influence of inherent vibration of the shaft, derived from a material of the shaft, a clamping position, a clamping strength, and the like.

Further, an impact method using a pendulum, such as the rigidity characteristic value measuring device of the first type, makes it difficult to stably strike the lowermost point due to characteristics of a head shape (due to a difference in FP value, etc.). This difference may make a striking position and an impact angle to vary and also make adjustment difficult.

When the rigidity characteristic value measuring device 20 of the second type is used as the rigidity characteristics measuring device 14 of the system 10 for measuring the rigidity characteristics, a CT value of a golf club head can be measured accurately in a short time.

As described above, according to the system 10 for measuring the rigidity characteristics according to the embodiment, the correlation data 12 between the CT value and the test velocity CT value is preliminarily calculated, and the representative CT value is estimated by measuring only the test velocity CT value at actual measurement. Accordingly, the representative CT value, which normally needs to be measured multiple times by changing the impact velocity, can be estimated by measurement at one test velocity, so the representative CT value can be measured in a short time.

The correlation data 12 is calculated for each product of an identical model, so it is advantageous for efficiently measuring representative characteristic values of a plurality of objects to be impacted, such as when total inspection is performed on mass-produced products.

The correlation data 12 is calculated for each reference impact position defined for respective products of an identical model, so it is advantageous for a case where one model has a plurality of management points (portions with a high possibility of falling out of the compatible range).

Whether a representative CT value of the golf club head 30 to be measured is within a compatible range is determined, and the determination result is presented, so it is advantageous for performing quality control on the object to be impacted.

The test velocity is defined as the test velocity range including the upper limit velocity and the lower limit velocity, so it is advantageous in that while a predetermined deviation is allowed with respect to the impact velocity of the impactor, the deviation is prevented from exceeding a range in which the correlation is available.

In particular, when the representative CT value is measured using the rigidity characteristic value measuring device of the first type having a structure in accordance with regulations and when the test velocity characteristic value is measured using the rigidity characteristic value measuring device of the second type that facilitates measurement, by each type of measurement, the representative CT value can be measured efficiently.

The invention claimed is:

1. A method for measuring rigidity characteristics configured to measure a rigidity characteristic value based on an acceleration occurring in an impactor when the impactor is caused to strike an object to be impacted, the method comprising the steps of:
1) Calculating a representative characteristic value of the object to be impacted based on the rigidity characteristic values measured multiple times by changing an impact velocity of the impactor;
2) Measuring a test velocity characteristic value, which is the rigidity characteristic value at the impact velocity set to a predetermined test velocity;
3) Calculating a correlation between the representative characteristic value and the test velocity characteristic value by performing the steps 1) and 2) on a plurality of objects to be impacted belonging to a group of objects to be impacted that are each predicted to have a substantially identical velocity dependence of the rigidity characteristic value;
4) Actually measuring the test velocity characteristic value for an other object to be impacted belonging to the group of objects to be impacted; and
5) Estimating the representative characteristic value of the other object to be impacted based on the test velocity characteristic value measured in the step 4) and the correlation calculated in the step 3).

2. The method for measuring the rigidity characteristics according to claim 1, wherein
the object to be impacted is a mass-produced product,
the group of objects to be impacted that are each predicted to have the substantially identical velocity dependence of the rigidity characteristic value are products of an identical model, and
in the step 3), the correlation is calculated for each of the products of the identical model.

3. The method for measuring the rigidity characteristics according to claim 2, wherein
the rigidity characteristic value is predicted to take a different value for each impact position of the impactor against the object to be impacted, and
in the step 3), the correlation is calculated for each reference impact position defined for corresponding each of the products of the identical model.

4. The method for measuring the rigidity characteristics according to claim 1, further comprising the step of:
6) Determining whether the representative characteristic value of the other object to be impacted, estimated in the step 5), is within the compatible range,
wherein a predetermined compatible range is set for the representative characteristic value.

5. The method for measuring the rigidity characteristics according to claim 4, further comprising the step of:
7) Presenting a determination result in the step 6) to a measurer.

6. The method for measuring the rigidity characteristics according to claim 1, wherein
the test velocity is defined as a test velocity range including an upper limit velocity and a lower limit velocity, and
in the step 4), measurement is performed at the impact velocity falling within the test velocity range.

7. The method for measuring the rigidity characteristics according to claim 6, wherein the test velocity is set to a lowest velocity of a plurality of the impact velocities in the step 1).

8. The method for measuring the rigidity characteristics according to claim 1, wherein
the rigidity characteristic value is measured by using a rigidity characteristic value measuring device,
in the step 1), the rigidity characteristic value is measured by using a rigidity characteristic value measuring device of a first type, and
in the steps 2) and 4), the rigidity characteristic value is measured by using a rigidity characteristic value measuring device of a second type different from the rigidity characteristic value measuring device of the first type.

9. The method for measuring the rigidity characteristics according to claim 8, wherein
the rigidity characteristic value measuring device of the first type is configured to cause the impactor to strike the object to be impacted using a pendulum, and
the rigidity characteristic value measuring device of the second type is configured to cause the impactor to strike the object to be impacted by dropping the impactor vertically.

10. The method for measuring the rigidity characteristics according to claim 1, wherein
the object to be impacted is a golf club head, and
the rigidity characteristic value is a CT value of the golf club head.

11. A system for measuring rigidity characteristics configured to measure a rigidity characteristic value of an object to be impacted based on an acceleration occurring in an impactor when the impactor is caused to strike the object to be impacted, the system comprising:
a rigidity characteristics measuring unit that measures correlation data between a representative characteristic value of the object to be impacted, which is calculated based on the rigidity characteristic values measured multiple times by changing an impact velocity of the impactor, and a test velocity characteristic value, which is the rigidity characteristic value at a predetermined test velocity set to the impact velocity, for each of a plurality of objects to be impacted belonging to a group of objects to be impacted that are each predicted to have a substantially identical velocity dependence of the rigidity characteristic value, and that measures the test velocity characteristic value for an other object to be impacted belonging to the group of objects to be impacted; and
a representative characteristic value estimation unit that estimates the representative characteristic value of the other object to be impacted based on the test velocity characteristic value measured by the rigidity characteristics measuring unit and the correlation data.

12. The system for measuring the rigidity characteristics according to claim 11, wherein
the object to be impacted is a mass-produced product, and
the group of objects to be impacted that are each predicted to have the substantially identical velocity dependence of the rigidity characteristic value are products of an identical model, and
the correlation data is calculated for each of the products of the identical model.

13. The system for measuring the rigidity characteristics according to claim 12, wherein
the rigidity characteristic value is predicted to take a different value for each impact position of the impactor against the object to be impacted, and
the correlation data is calculated for each reference impact position defined for corresponding each of the models.

14. The system for measuring the rigidity characteristics according to claim 11, further comprising:
a compatibility determination unit that determines whether the representative characteristic value of the other object to be impacted, estimated by the representative characteristic value estimation unit, falls within the compatible range,
wherein a predetermined compatible range is set for the representative characteristic value.

15. The system for measuring the rigidity characteristics according to claim 14, further comprising:
a determination result presenting unit that presents a determination result in the compatibility determination unit to a measurer.

16. The system for measuring the rigidity characteristics according to claim 11, wherein
the test velocity is defined as a test velocity range including an upper limit velocity and a lower limit velocity, and
the rigidity characteristics measuring unit performs measurement at the impact velocity falling within the test velocity range.

17. The system for measuring the rigidity characteristics according to claim 16, wherein the test velocity is set to a lowest velocity of a plurality of the impact velocities when the representative characteristic value is calculated.

18. The system for measuring the rigidity characteristics according to claim 11, wherein
the representative characteristic value of the correlation data is measured by using a rigidity characteristic value measuring device of a first type, and the test velocity characteristic value of the correlation data is measured by using a rigidity characteristic value measuring device of a second type different from the rigidity characteristic value measuring device of the first type, and
the rigidity characteristics measuring unit is the rigidity characteristic value measuring device of the second type.

19. The system for measuring the rigidity characteristics according to claim 18, wherein
the rigidity characteristic value measuring device of the first type has a mechanism of causing the impactor to strike the object to be impacted using a pendulum, and
the rigidity characteristic value measuring device of the second type has a mechanism of causing the impactor to strike the object to be impacted by dropping the impactor vertically.

20. The system for measuring the rigidity characteristics according to claim 11, wherein
the object to be impacted is a golf club head, and
the rigidity characteristic value is a CT value of the golf club head.

* * * * *